United States Patent
Awasthi

(10) Patent No.: US 11,427,816 B2
(45) Date of Patent: Aug. 30, 2022

(54) CANCER TREATMENT THROUGH RLIP76 PARTIAL DEPLETION

(71) Applicant: BOARD OF REGENTS, THE UNIVERSITY OF TEXAS SYSTEM, Austin, TX (US)

(72) Inventor: Sanjay Awasthi, Lubbock, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/684,508

(22) Filed: Aug. 23, 2017

(65) Prior Publication Data

US 2019/0062727 A1 Feb. 28, 2019

(51) Int. Cl.
| | |
|---|---|
| *A61K 39/395* | (2006.01) |
| *C12N 15/10* | (2006.01) |
| *C12N 11/18* | (2006.01) |
| *C12N 15/11* | (2006.01) |
| *C12N 5/09* | (2010.01) |
| *C07K 16/40* | (2006.01) |
| *C12N 15/113* | (2010.01) |
| *A61P 35/00* | (2006.01) |
| *C12N 9/00* | (2006.01) |

(52) U.S. Cl.
CPC .......... *C12N 15/1024* (2013.01); *A61P 35/00* (2018.01); *C07K 16/40* (2013.01); *C12N 5/0693* (2013.01); *C12N 11/18* (2013.01); *C12N 15/11* (2013.01); *C12N 15/113* (2013.01); *C07K 2317/34* (2013.01); *C07K 2317/73* (2013.01); *C12N 9/00* (2013.01); *C12N 2310/11* (2013.01); *C12N 2310/14* (2013.01); *C12N 2310/315* (2013.01)

(58) Field of Classification Search
CPC combination set(s) only.
See application file for complete search history.

(56) References Cited

U.S. PATENT DOCUMENTS

| | | | |
|---|---|---|---|
| 2006/0104983 A1 | 5/2006 | Awasthi et al. | |
| 2014/0065207 A1* | 3/2014 | Awasthi | C07K 14/705 424/450 |
| 2017/0059556 A1 | 3/2017 | Awasthi et al. | |

OTHER PUBLICATIONS

Granziero et al, Eur. J. Immunol. 29:1127-1138, 1999.*
Byers, T, CA Journal, vol. 49, No. 6, Nov./Dec. 1999.*
Singhal et al, Cancer Prev Res: 4:879-889, 2011.*
Sorrell et al, Mol Diagn Ther, 17:31-47, 2013.*
Singhal et al. Partial knockdown of RLIP76 prevents cancer susceptibility of p53 null mice. In: Proceedings of the American Association for Cancer Research Annual Meeting 2017. Cancer Res, Jul. 2017, vol. 77, No. 13 Suppl.
Pantziarka et al. Li Fraumeni syndrome, cancer and senescence: a new hypothesis. A Cancer Cell International, Apr. 15, 2013, vol. 3, No. 35, pp. 1-6.
Tovy et al. p53 is essential for DNA methylation homeostasis in naive embryonic stem cells, and its loss promotes clonal heterogeneity. Genes Dev., May 15, 2017, vol. 31, No. 10, pp. 959-972.
International Search Report in related PCT/2018/046036 dated Jan. 8, 2019.

* cited by examiner

*Primary Examiner* — Mark Halvorson
(74) *Attorney, Agent, or Firm* — Norton Rose Fulbright US LLP

(57) ABSTRACT

Partial depletion of RLIP76 in p53 deficient living subject has shown many health benefits. In one embodiment, partical Rlip depletion is used to prevent or treat cancer in p53 deficient living subjects. In another embodiment, partial Rlip depletion is used for reversion of DNA-methylation abnormalities caused by the lack of p53 to normal in p53 deficient living subjects. In yet another embodiment, partial Rlip depletion is used in reduction of blood glucose, insulin-resistance, hyperlipidemina, or any combination thereof in p53 deficient living subjects. Methods of using liposome containing anti-sense nucleic acid or double stranded siRNA to partially deplete RLIP76 and thus treat p53 deficient subject are disclosed. The approaches described herein can be especially helpful in preventing cancer in Li-Fraumeni patients.

13 Claims, 3 Drawing Sheets

Specification includes a Sequence Listing.

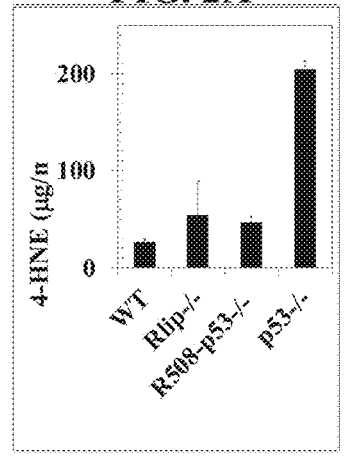
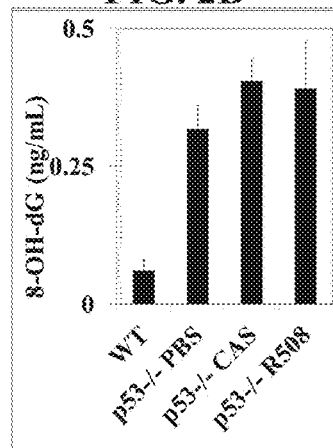
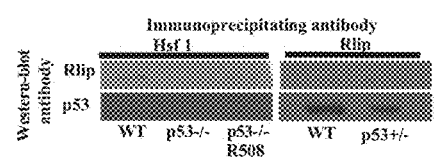
FIG. 2A
FIG. 2B
FIG. 2C
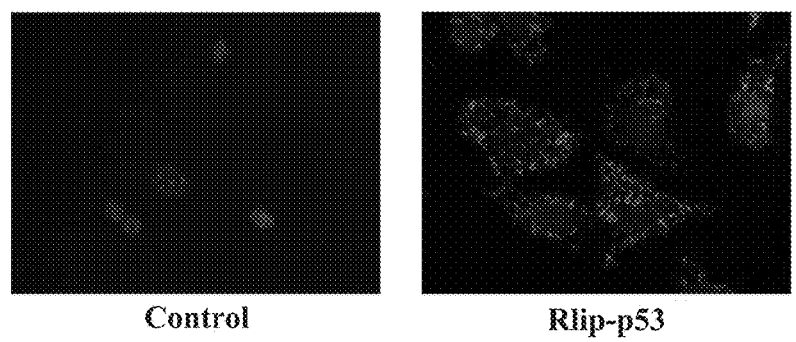
FIG. 2D
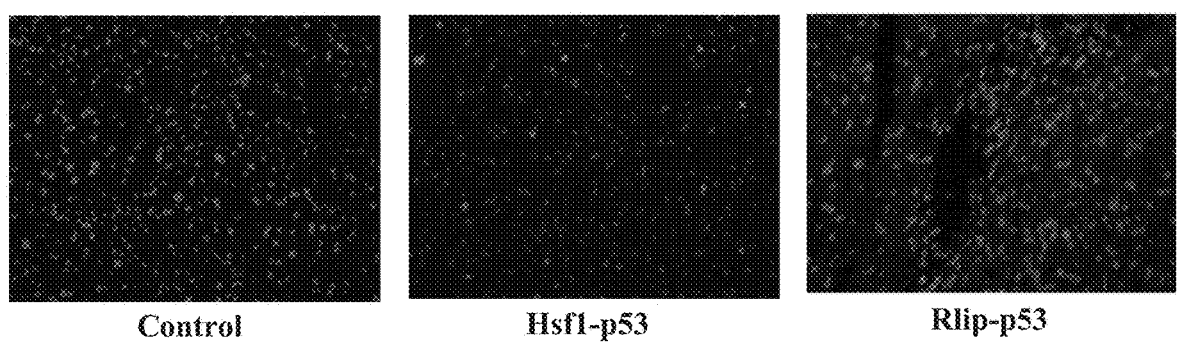
FIG. 2E

CANCER TREATMENT THROUGH RLIP76 PARTIAL DEPLETION

STATEMENT OF GOVERNMENT SUPPORT

This invention was made with government support under grant number P30CA33572 awarded by the City of Hope National Medical Center and its Cancer Center Support Grant from the National Cancer Institute of the National Institutes of Health. The government has certain rights in the invention.

STATEMENT REGARDING SEQUENCE LISTING

The Sequence Listing associated with this application is part of the description and is provided in the form of an Annex C/ST.25 text file in lieu of a paper copy, and hereby incorporated by reference into the specification. The name of the text file containing the Sequence Listing is 21001706SequenceListing.txt.txt. The text file is 4 kb, was created on Aug. 23, 2017, and is being submitted electronically via EFS-Web.

FIELD OF THE INVENTION

The present disclosure is directed to methods of treating or preventing cancer in p53 deficient patients. In one embodiment, the patient has Li-Fraumeni syndrome. The method comprises the step of at least partially depletes RLIP76 in the patient.

BACKGROUND

The p53 protein (human TP53 gene) is a 53 kDa stress-responsive, genome protective, tumor suppressor protein that loses its normal function due to genetic alterations found in most cancers. The powerful tumor suppressor function of p53 is evident from the universal susceptibility of p53 knockout mice to spontaneous cancer within 6 months of age, usually T-cell lymphoma and the inability to abrogate this phenotype with any previous genetic modifications. The pathogenic role of loss of p53 function in spontaneous neoplasia in humans is evident in Li-Fraumeni syndrome (LFS), an autosomal dominant genetic disorder of p53 deficiency which carries a lifetime cancer risk of 70% in men and approaching 100% in women. Surveillance is the only effective means to prevent death from malignancy. Deficiency of p53 function in sporadic cancers is associated with treatment failure due to dysregulated expression of p53-linked stress response genes that protect cancer cells from apoptosis and provide metabolic defenses against oxidative stress and xenobiotic toxins such as chemotherapy drugs. There remains a need to prevent or treat patients who suffer from p53 deficiency related cancer, such as Li-Fraumeni patients.

SUMMARY

In a first aspect, provided herein are methods of preventing or treating cancer in a p53 deficient living subject. The method comprises administering an effective amount of a composition into the living subject to partially deplete RLIP76 in the living subject, wherein the composition comprises a compound that partially depletes RLIP76. In one embodiment, the compound is a liposome anti-sense nucleic acid that has the nucleic acid sequence of SEQ ID NO.: 2 that targets the nucleotides encoding a region of RLIP76 having a sequence of SEQ ID NO.: 1. In another embodiment, the compound is a liposome double stranded siRNA molecule having a sequence of SEC ID NO: 3 that targets the nucleotides encoding a region of RLIP76 having a sequence of SEQ ID NO.: 1. In one embodiment, the compound is a liposome anti-sense nucleic acid that is complementary to an mRNA that encodes SEQ ID NO.:4 and the nucleic acid targets nucleotides encoding a region of RLIP76 having a sequence of SEQ ID NO.: 1. In another embodiment, the compound is an anti-Rlip antibody. In one embodiment, the living subject is a human. The composition may further comprise a pharmaceutically acceptable carrier. The composition administration can be repeated at predetermined intervals to effect chronical partial depletion of RLIP76 in the living subject such that the cancer treatment or prevention can be sustained chronically.

In a second aspect, provided herein is a method of preventing or treating cancer in a Li-Fraumeni patient. The method comprises administering an effective amount of a composition into the patient to partially deplete at least 25% of RLIP76 in the patient, wherein the composition comprises a compound that at least partially depletes RLIP76 in the patient. In one embodiment, the compound is a liposome anti-sense nucleic acid that has the nucleic acid sequence of SEQ ID NO.: 2 that targets the nucleotides encoding a region of RLIP76 having a sequence of SEQ ID NO.: 1. In another embodiment, the compound is a liposome double stranded siRNA molecule having a sequence of SEC ID NO: 3 that targets the nucleotides encoding a region of RLIP76 having a sequence of SEQ ID NO.: 1. In one embodiment, the compound is a liposome anti-sense nucleic acid that is complementary to an mRNA that encodes SEQ ID NO.:4 and the nucleic acid targets the nucleotides encoding a region of RLIP76 having a sequence of SEQ ID NO.: 1. In another embodiment, the compound is an anti-Rlip antibody. The composition may further comprise a pharmaceutically acceptable carrier. The composition administration can be repeated at predetermined intervals to effect chronical partial depletion of RLIP76 in the living subject such that the cancer treatment or prevention can be sustained chronically.

In a third aspect, provided herein is a method of reducing blood glucose, insulin resistance, hyperlipidemia, or any combination thereof by at least 50% in a living subject, for example by: 50-55%, 55-60%, 60-65%, 65-70%, 70-75%, 75-80%, 80-85%, 85-90%, 90-95%, 95-98%, 98-99% or to normal. The method comprises administering an effective amount of a composition into the living subject to at least partially deplete RLIP76 in the living subject, wherein the composition comprises a compound that at least partially depletes RLIP76 in the living subject. The compound can be a liposome anti-sense nucleic acid that has the nucleic acid sequence of SEQ ID NO.: 2, a liposome anti-sense nucleic acid that is complementary to an mRNA that encodes SEQ ID NO.:4, and a liposome double stranded siRNA molecule having a sequence of SEC ID NO: 3 that targets the nucleotides encoding a region of RLIP76 having a sequence of SEQ ID NO.: 1. In one embodiment, the compound is an anti-Rlip antibody. The composition may further comprise a pharmaceutically acceptable carrier. In one embodiment, the living subject is a human. The composition administration can be repeated at predetermined intervals to effect chronical partial depletion of RLIP76 in the living subject such that reduction of blood glucose, insulin resistance, hyperlipidemina, or any combination thereof in a patient can be sustained chronically.

In a fourth aspect, provided herein is a method for reversion of DNA-methylation abnormalities caused by the lack of p53 by at least 50% in a p53 deficient living subject, for example by at least: 55%, 60%, 65%, 70%, 75%, 80%, 85%, 90%, 95%, 98%, or 99%. The method comprises administering an effective amount of a composition into the living subject to at least partially deplete RLIP76 in the living subject, wherein the composition comprises a compound that at least partially depletes RLIP76 in the living subject. The compound can be a liposome anti-sense nucleic acid that has the nucleic acid sequence of SEQ ID NO.: 2, a liposome anti-sense nucleic acid that is complementary to an mRNA that encodes SEQ ID NO.:4, and a liposome double stranded siRNA molecule having a sequence of SEC ID NO: 3 that targets the nucleotides encoding a region of RLIP76 having a sequence of SEQ ID NO.: 1. In one embodiment, the compound is an anti-Rlip antibody. The composition may further comprise a pharmaceutically acceptable carrier. In one embodiment, the living subject is a human. The composition administration can be repeated at predetermined intervals to effect chronical partial depletion of RLIP76 in the living subject such that the reversal of DNA-methlation abnormalities caused by the lack of p53 in a patient can be sustained chronically.

BRIEF DESCRIPTION OF THE DRAWINGS

The drawing figures are not necessarily to scale and certain features may be shown exaggerated in scale or in a somewhat generalized or schematic form in the interest of clarity and conciseness. For more complete understanding of the features and advantages of the present invention, reference is now made to the detailed description of the invention along with the accompanying figures, wherein:

FIG. 2A shows 4-hydroxynonenal (4HNE) levels in liver homogenate of wt, Rlip R508 treated $p53^{-/-}$ and $p53^{-/-}$ mice.

FIG. 2B shows 8-OH-deoxyguanosine (8OHdG) levels in liver homogenate of wt, PBS, CAS, and R508 treated $p53^{-/-}$ mice.

FIG. 2C shows results of co-immunoprecipitation studies in whole cell homogenates of wt and p53 knockout MEFs without or with treatment with R508.

FIG. 2D shows interactions between Rlip and p53 in cultured wt MEF by proximity ligation assays (PLA) with Rlip antibody omitted in control sample.

FIG. 2E shows interactions between Rlip and p53, p53 and HSF1 in 5 μm liver tissue sections by PLA with p53 antibody omitted in control sample.

DETAILED DESCRIPTION

Definitions

Figure 1A:
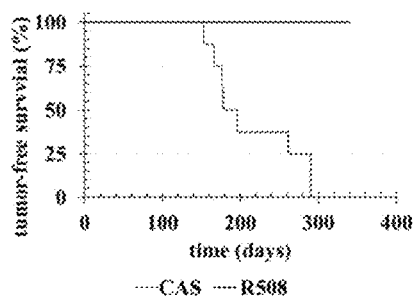
FIG. 1A shows tumor free-survival curve of $p53^{-/-}$ mice treated weekly with CAS or R508 for up to 24 weeks.

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a composition that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. In some embodiments, the subject is a mammal such as a primate, for example, a human.

"Amount effective" and "effective amount" in the context of a composition or dosage form for administration to a subject refers to an amount of the composition or dosage form that produces one or more desired responses in the subject, for example, prevent cancer in p53 deficient patients. Therefore, in some embodiments, an amount effective is any amount of a composition provided herein that produces one or more of these desired responses. The amount is one that a clinician believes to have a clinical benefit for a p53 deficient subject in need of cancer prevention or treatment.

Effective amount can involve only improving the patient's condition, although in some embodiments, it involves restoring patient's condition. An amount that is effective can also be an amount of a composition provided herein that produces a desired therapeutic endpoint or a desired therapeutic result. Effective amount result in cancer treatment or prevention in a subject after the administration of the compositions disclosed herein. The achievement of any of the foregoing are monitored by routine methods.

In some embodiments of any of the compositions and methods provided, the effective amount is one in which the subject is symptom free, such as cancer free, has reversed DNA-methylation abnormalities to normal for at least 1 week, at least 2 weeks, at least 1 month, at least 2 months, at least 3 months, at least 4 months, at least 5 months, at least 6 months, at least 9 months, at least 1 year, at least 2 years, at least 5 years, or longer. In other embodiments of any of the compositions and methods provided, the effective amount is one which produces a measurable desired response, for example, a measurable decrease or disappearance of cancer in the patient for at least 1 week, at least 2 weeks, at least 1 month, at least 2 months, at least 3 months, at least 4 months, at least 5 months, at least 6 months, at least 9 months, at least 1 year, at least 2 years, at least 5 years, or longer.

Effective amount will depend, of course, on the particular subject being treated; the severity of a condition, disease or disorder; the individual patient parameters including age, physical condition, size and weight; the duration of the treatment; the nature of concurrent therapy (if any); the specific route of administration and like factors within the knowledge and expertise of the health practitioner. The effective amount can be 0.1-30 mg per kg of a living subject, for example, 0.1-0.2 mg/kg, 0.2-0.3 mg/kg, 0.3-0.4 mg/kg, 0.4-0.5 mg/kg, 0.5-0.6 mg/kg, 0.6-0.7 mg/kg, 0.7-0.8 mg/kg, 0.8-0.9 mg/kg, 0.9-1 mg/kg, 1-2 mg/kg, 2-3 mg/kg, 3-4 mg/kg, 4-5 mg/kg, 5-6 mg/kg, 6-7 mg/kg, 7-8 mg/kg, 8-9 mg/kg, 9-10 mg/kg, 10-11 mg/kg, 11-12 mg/kg, 12-13 mg/kg, 13-14 mg/kg, 14-15 mg/kg, 15-16 mg/kg, 16-17 mg/kg, 17-18 mg/kg, 18-19 mg/kg, 19-20 mg/kg, 20-21 mg/kg, 21-22 mg/kg, 22-23 mg/kg, 23-24 mg/kg, 24-25 mg/kg, 25-26 mg/kg, 26-27 mg/kg, 27-28 mg/kg, 28-29 mg/kg, 29-30 mg/kg, 1.5-25 mg/kg, 2-20 mg/kg, 2.5-15 mg/kg, 3-10 mg/kg, or 4-7 mg/kg.

The partial depletion of Rlip disclosed herein means at least 20% of the total Rlip present in a living subject has been inactivated or inhibited, for example 20-22.5%, 22.5-25%, 22.5-27.5%, 27.5-30%, 30-32.5%, 32.5-35%, 35-37.5%, 37.5-40%, 40-42.5%, 42.5-45%, 45-47.5%, 47.5-50%, 50-52.5%, 52.5-55%, 55-57.5%, 57.5-60%, 60-62.5%, 62.5-65%, 65-67.5%, 67.5-70%, 70-72.5%, 72.5-75%, 75-77.5%, or 77.5-80%.

The predetermined interval to effect chronical treatment results means every day to every year, for example, every two days, every three days, every four days, every five days, every six days, every week, every 1.5 week, every two weeks, every 2.5 weeks, every three weeks, every 3.5 weeks, every 4 weeks, every 5 weeks, every 6 weeks, every 7 weeks, every 8 weeks, every 9 weeks, every 10 weeks, every 11 weeks, every 12 weeks, every 13 weeks, every 14 weeks, every 15 weeks, every 16 weeks, every 17 weeks, every 18 weeks, every 19 weeks, every 20 weeks, every 21 weeks, every 22 weeks, every 23 weeks, every 24 weeks, every 25 weeks, every 26 weeks, every 27 weeks, every 28 weeks, every 29 weeks, every 30 weeks, every 31 weeks, every 32 weeks, every 33 weeks, every 34 weeks, every 35 weeks, every 36 weeks, every 37 weeks, every 38 weeks, every 39 weeks, every 40 weeks, every 41 weeks, every 42 weeks, every 43 weeks, every 44 weeks, every 45 weeks, every 46 weeks, every 47 weeks, every 48 weeks, every 49 weeks, every 50 weeks, every 51 week, or every 52 weeks.

"Dosage form" means a pharmacologically and/or immunologically active material in a medium, carrier, vehicle, or device suitable for administration to a subject.

"Pharmaceutically acceptable excipient" means a pharmacologically inactive material used together with the liposomes disclosed herein and carriers to formulate the compositions disclosed herein. Pharmaceutically acceptable excipients comprise a variety of materials known in the art, including but not limited to saccharides (such as glucose, lactose, and the like), preservatives such as antimicrobial agents, reconstitution aids, colorants, saline (such as phosphate buffered saline), and buffers.

As used herein, a "proteoliposome" is generally a protein and lectin or glyco- or phospholipid combination that forms a spherical micellular-like or vesicular structure. The structures may form spontaneously or by chemical or mechanical manipulation, or combinations thereof. Proteoliposomes take advantage of the amphipathic nature of the lipid (or lectin) that causes them to form bilayers when in solution resulting in at least one of several shapes, including: (a) spherical micelle with the tails inward, or (b) bimolecular sheets that are bilayers with hydrophobic tails sandwiched between hydrophilic head groups. In general, proteoliposomes may reseal themselves when torn or broken. Proteoliposomes may contain only one lectin or lipid or a variety and combination of each. Examples of phospholipids include phosphatidylcholine, sphingomyelin, phosphatidylserine, inositol phospholipids, and phosphatidylethanolamine. When used, proteoliposomes may be charged or electrically neutral and are generally used at physiological pH. They may also be structures mixed with detergent (e.g., detergent/lipid/protein, detergent/lectin/protein). Methods for preparing proteoliposomes of defined lipid-protein or lectin-protein ratios and size are well-known to one of ordinary skill in the art of molecular biology and protein/lipid biochemistry.

Abbreviations used are defined as follows: TP53: tumor protein 53, referred to herein as p53; RLIP76: 76 kDa splice variant protein encoded by the human RALBP1 gene (18p11.22), originally identified as dinitrophenyl S-glutathione ATPase (DNP-SG ATPase), is referred to herein as Rlip; CAS: control antisense; R508: Rlip-antisense; GS-E: GSH-electrophile conjugate; CDE: clathrin-dependent endocytosis; 4-HNE: 4-hydroxy-trans-2-nonenal; GS-HNE: thioether of GSH and 4-HNE; B[a]P: benzo[a]pyrene; WGBS: whole-genome bisulfate sequencing; 8OHdG: 8-hydroxydeoxyguanosine; PLA: proximity ligation assay; DAVID: Database for Annotation, Visualization and Integrated Discovery; GO: gene ontology; KEGG: Kyoto Encyclopedia of Genes and Genomes; IPA: Integrated Pathways Analysis; RPKM: reads per kilobase of transcript per million mapped reads; SINE/LINE: small and large interspersed nuclear elements; MEF: mouse embryonic fibroblast; FGF: fibroblast growth factor; HSF1: heat shock factor 1; DMR: differentially methylated regions. The gene name abbreviations used are according to official gene nomenclature (http://www.genecards.org).

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

The present disclosure may be understood more readily by reference to the following detailed description of embodiments and to the Figures and their previous and following description.

General

Disclosed herein are methods of preventing cancer in a TP53 (p53) deficient living subject. Rlip deficiency strongly inhibited spontaneous as well as benzo[a]pyrene-induced carcinogenesis in $p53^{-/-}$ mice. Rlip deficiency induced by weekly administration of an Rlip-specific phosphorothioate antisense molecule, R508, effectively prevented methylomic and transcriptomic abnormalities found in cancer-bearing $p53^{-/-}$ mice. R508-treated cancer-free $p53^{-/-}$ mice had reduced expression of genes associated with inflammation, immune activation, stem cell maintenance, and cancer. Abnormalities of gene promoter methylation found in cancer bearing $p53^{-/-}$ mice were nearly absent in R508-treated mice. Cancer suppression by Rlip depletion was not associated with reduction in oxidative DNA damage, indicating that Rlip regulates late events in malignant transformation. The efficiency with which Rlip deficiency suppresses spontaneous malignancy in $p53^{-/-}$ mice has not been observed with any previously reported pharmacological or genetic intervention. The methods disclosed herein offer tumor suppression in p53 deficient living subject. For example, a method for suppression of spontaneous malignancy in hereditary cancer syndromes such as Li-Fraumeni is disclosed herein.

Rlip (encoded by RALBP1 [18p11.22]) is a stress-responsive ATPase enzyme of the mercapturic acid pathway that catalyzes the transmembrane efflux of the exogenous (xenobiotic) and endogenous (lipid-hydroperoxide-derived alkenal) electrophilic toxins after glutathione S-transferases (GSTs) catalyze the formation of GSH-electrophile thioether conjugates (GS-E) (9-33). Its ATPase activity is coupled with clathrin-dependent endocytosis (CDE), the RAL-regulated first step in the internalization, trafficking, and recycling of membrane vesicles that contain membrane receptors bound to a broad array of extracellular ligands that promote cancer. CDE regulates signaling down-stream of receptors for insulin, EGF, TNFα, FGF1 and many other peptide hormones; Rlip, a key component of CDE, links RAL, RAS, RHO and RAC signaling. CDE as well as GS-E transport are severely deficient (<80%) in $Rlip^{-/-}$ mice. Rlip regulates the activity of upstream mercapturic acid pathway enzymes that metabolize xenobiotic and endogenous electrophiles by preventing product/feedback-inhibition exerted by GS-E. Oxidative metabolism of ω-6 polyunsaturated fatty acids in response to radiant (x-ray, UV light, heat) or oxidative stress yields lipid hydroperoxides, which degrade to toxic lipid alkenals, principally 4-hydroxynonenal (4HNE). 4HNE is metabolized primarily to a glutathione conjugate (GS-HNE) that is removed from cells by Rlip. Recombinant Rlip protein is the most potent biological agent for defending cells and animals from toxicity of stressors that generate massive amounts of 4HNE, ionizing radiation, and chemical warfare agents. Interestingly, the apoptotic activity of 4HNE is directed selectively towards malignant cells, evident from apoptosis of cancer cells and dramatic regression of melanoma, neuroblastoma, and cancers of the lung, colon, kidney, pancreas, and prostate in mouse models. An existential need of cancer cells for Rlip is underscored by resistance to chemical carcinogenesis in $Rlip^{-/-}$ mice to a degree exceeding that for any other previously reported genetic intervention.

TP53 (p53) functions as a stress-responsive, genome protective, tumor suppressor whose functions are lost or altered in most malignancies. p53 homozygous knockout ($p53^{-/-}$) mice uniformly die of spontaneous malignancy, typically T-cell lymphoma. RALBP1 (RLIP76, Rlip) is a stress-protective, mercapturic acid pathway transporter protein that also functions as a Ral-effector involved in clathrin-dependent endocytosis. In stark contrast to $p53^{-/-}$ mice, $Rlip^{-/-}$ mice are highly resistant to carcinogenesis. The relationship between Rlip and p53 in carcinogenesis has been found to be functionally opposed as further described below. Although $p53^{-/-}$ mice are used as examples throughout the present disclosure, it is believed that the observation made on $p53^{-/-}$ mice can be extrapolated to other living subjects that suffer from p53 deficiency, for example cancer patients who suffers from p53 deficiency.

Rlip Deficiency Suppresses Malignancy in $p53^{-/-}$ Mice

Figure 1B:
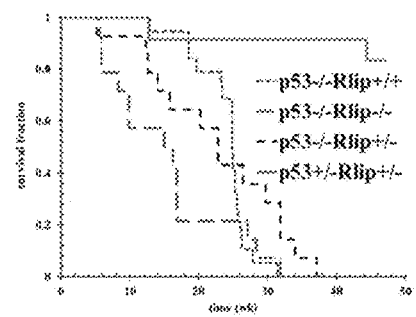
FIG. 1B shows overall survival curves of double-knockout mice of the indicated genotype.
Figure 1C:
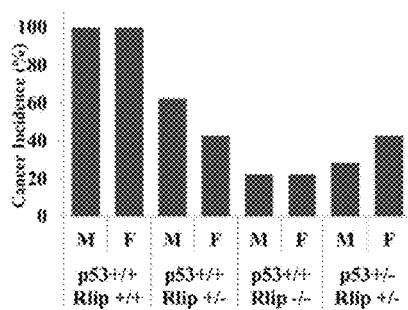
FIG. 1C shows cancer incidence in mice of the indicated genotypes administered with benzo[a]pyrene.

A single 200 μg intraperitoneal dose of R508 given to wt mice reduced Rlip protein to 56±12% of control in the liver, and to a lesser extent in all other tissues, at 24 h (p<0.001), with gradual recovery to 91±4% (p=ns) at day 7. Reduction of blood glucose by 26%, triglycerides by 32%, and cholesterol by 48% upon R508 treatment showed expected pharmacodynamic effects, given that these metabolic alterations are characteristic of Rlip knockout mice. Treatment of C57B1/6 $p53^{-/-}$ mice with weekly intraperitoneal injections of 200 μg R508 or control scrambled antisense (CAS) beginning at age 8 weeks reduced Rlip protein to 47±7% (p<0.0001) and Rlip mRNA to 49±13% (p<0.001), and prevented malignancy in 100% of R508-treated $p53^{-/-}$ mice, whereas all control mice died of T-cell lymphomas before 24 weeks of age as shown in FIG. 1A. CAS-treated mice had extensive tissue injury in multiple organs whereas R508-treated $p53^{-/-}$ mice had no histological evidence of tissue injury or any type of malignancy. All $p53^{+/-} Rlip^{+/-}$ offspring from cross-breeding $Rlip^{+/-}$ and $p53^{+/-}$ were free of malignancy, with 11/13 alive, healthy and cancer-free at necropsy at 48-week age; 2/13 sacrificed at earlier ages due to malocclusion were also cancer free as shown in FIG. 1B. Only male $p53^{-/-}/Rlip^{-/-}$ and female $p53^{-/-} Rlip^{+/-}$ were viable but developed inanition due to malocclusion or hydrocephalus at a median age of 12 and 23 weeks, respectively, but were also all free of malignancy at necropsy. In a chemical carcinogenesis model, 75% of male and 60% of female $p53^{+/-}/Rlip^{+/-}$ mice treated with B[a]P were free of any malignancy at 6-month age, whereas all wild-type ($p53^{+/+}Rlip^{+/+}$) mice developed stomach or lung adenocarcinoma as shown in FIG. 1C. Only 60% of $p53^{+/+}Rlip^{+/-}$ males and 40% of females developed adenocarcinoma; this rate was intermediate between wild-type (100%) and $p53^{+/+}$ $Rlip^{-/-}$ (20%) previously reported. Thus, hemizygous Rlip deficiency also exerted a strong dominant negative effect on the spontaneous malignancy phenotype of $p53^{-/-}$ mice.

The Transcriptome of R508-treated $p53^{-/-}$ Mice Resembled Wild-Type

Figure 1D:
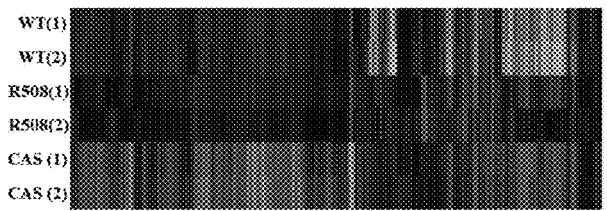
FIG. 1D shows heat map of hierarchical clustering of RNA-Seq samples of wt, R508 treated, and CAS treated $p53^{-/-}$ mice.

The hepatic transcriptome of R508 and CAS-treated $p53^{-/-}$ mice were compared using RNA-Seq. The RNA-Seq results were validated by results of qRT-PCR (Pearson R=0.876, p<0.0001). Unsupervised hierarchical clustering analyses of RNA-Seq results on hepatic tissues revealed that the transcriptome of R508 treated $p53^{-/-}$ mouse was very similar to wt as shown in FIG. 1D. Gene ontology (GO) and KEGG pathways terms showed differential expression of cell cycling, T-cell immunity, inflammation, cancer, developmental and stem cell processes in control p53$^{-/-}$ mice, consistent with previous reports. The change in z-scores of differentially expressed pathways between R508 vs. CAS-treated p53$^{-/-}$ mice was essentially opposite that between p53$^{-/-}$ vs. wt mice: the majority pathways up- or down-regulated in control p53-/- mice were normalized towards wt in the R508-treated p53$^{-/-}$ mice. Indeed, the direction of change in the z-score in many top differentially expressed pathways caused by R508 resembled that between Rlip$^{-/-}$ vs. wt or Rlip$^{+/-}$ vs. wt, providing strong evidence for target specificity of R508. The transcriptomes of young (9-week) p53$^{-/-}$ or wt were quantitatively similar to aged (32-week) wt mice, and distinct from cancer-bearing aged p53$^{-/-}$ mice, indicating that the abnormal transcriptome of p53$^{-/-}$ mice was not congenital but acquired, either due to aging or as a consequence of a lymphoma-induced cytokine storm.

Figure 1E:
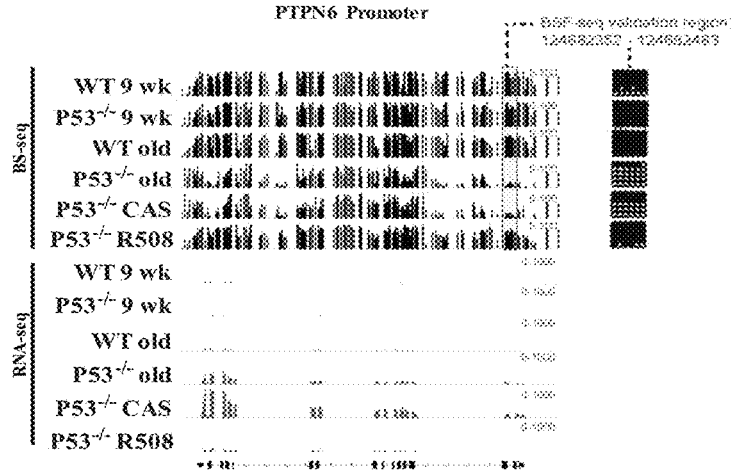
FIG. 1E shows analysis results of WGBS (BS-Seq) performed on liver tissues within PTPN6 gene promoter.
Figure 1F:
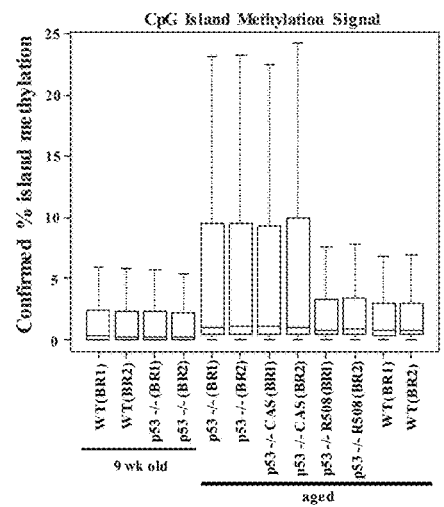
FIG. 1F shows total CpG island methylation compared between PBS, CAS, or R508-treated p53−/− mice, young (9 week) wt or p53−/− mice, and aged wt mice.

DNA-Methylation Abnormalities of p53$^{-/-}$ Mice were Corrected by Rlip Depletion Considering that the dramatic switch in the transcriptome of R508-treated p53$^{-/-}$ mice could be mediated through epigenetic mechanisms known to be involved in malignancy, we conducted whole-genome bisulfite sequencing (WGBS). Conventional bisulfite sequencing (CBS) and alignment with RNA-Seq results confirmed the validity of WGBS results and indicated a close correlation between the transcriptomic and methylomic changes that occur in p53$^{-/-}$ mice with age and carcinogenesis. This is depicted in representative examples for PTPN6 gene as show in FIG. 1E and HOXA5 genes (data not shown). The relationship of parallel methylomic and transcriptomic alterations was also evident in several other genes, for example the HOXA-D cluster, LST1, LTB, TNF, LTA, KLF4, CDKN2A, MYC as well as in the residual TP53 gene (data not shown). Hierarchical clustering analyses revealed that the methylome of cancer-bearing PBS or CAS-treated p53-/- mice was clearly distinct from the R508-treated p53$^{-/-}$ mice, which closely resembled young or aged wt mice and the young p53$^{-/-}$ mice as shown in FIG. 1F. Whereas 14,367 differentially methylated regions (DMR) were found between p53$^{-/-}$ vs. wt, only 869 DMR were found between R508-treated p53$^{-/-}$ vs. wt mice: approximately 95% of all methylation abnormalities were prevented by Rlip depletion as shown in Table 1 below.

CpG island hypermethylation, repetitive element (SINE/LINE) hypomethylation, and gains or losses of DNA methylation in promoters and gene-bodies of key cancer developmental genes in p53$^{-/-}$ were also prevented by R508. Promoter hypomethylation of critical immune system genes involved in leukocyte activation, T cell proliferation, and cytokine production found in control p53$^{-/-}$ was essentially absent in R508-treated p53$^{-/-}$ mice. Compared with 31 hypermethylated DMRs in promoters of genes within the ontology term embryonic morphogenesis (including HOXA-D clusters), only 3 were hypermethylated in R508-treated p53$^{-/-}$ mice. Ontology terms related to Rlip function enriched in R508 treated p53$^{-/-}$ mice included GSH metabolism, xenobiotic metabolism, oxidative stress, transport, endocytosis, vesicular transport, mitochondrial abnormalities, cell cycling, mitosis, PI3K and MAPK signaling, angiogenesis and cancer pathways. Reduced representation bisulfite sequencing of DNA from wt and p53$^{-/-}$ MEF in cell culture revealed over 15,000 DMRs. Because the lymphoma-associated cytokine storm present in the control p53$^{-/-}$ mice was absent in cultured MEF, accelerated accumulation of methylomic aberration appeared to be a function of p53 deficiency itself rather than simply a consequence of lymphoma.

TABLE 1

DNA Methylation Comparison of wt, Rlip$^{-/-}$ and CAS vs. R508-treated p53$^{-/-}$ mice[1]

| Sample Comparison | Methylation Change | Promoter | Intragenic | Intergenic | Total |
|---|---|---|---|---|---|
| wt vs. Rlip$^{-/-}$ (32 wk) | Hyper | 2 | 23 | 39 | 64 |
|  | Hypo | 1 | 7 | 10 | 18 |
| wt (9 wk vs. aged) | Hyper | 5 | 33 | 23 | 61 |
|  | Hypo | 27 | 134 | 69 | 230 |
| wt vs. p53$^{-/-}$ (9 wk) | Hyper | 32 | 106 | 92 | 230 |
|  | Hypo | 10 | 71 | 48 | 129 |
| p53$^{-/-}$ CAS vs. PBS (aged) | Hyper | 8 | 26 | 25 | 59 |
|  | Hypo | 4 | 16 | 11 | 31 |
| p53$^{-/-}$ CAS vs. R508 (aged) | Hyper | 1177 | 3869 | 2600 | 7646 |
|  | Hypo | 364 | 3717 | 2640 | 6721 |
| P53$^{-/-}$ CAS vs. wt (aged) | Hyper | 1523 | 6561 | 4375 | 12459 |
|  | Hypo | 595 | 5403 | 3996 | 9994 |
| P53$^{-/-}$-R508 vs. wt (aged) | Hyper | 37 | 298 | 201 | 536 |
|  | Hypo | 32 | 165 | 136 | 333 |

[1]All mm9 Refseq mRNAs were considered in the annotation. There were totally >21 million CpG sites analyzed. Results indicate almost no difference between wt and Rlip$^{-/-}$, and the CAS-treated p53$^{-/-}$ methylome has more sites loss of methylation than gain of methylation. A small but significant number of regions of methylation loss or gain in p53$^{-/-}$ were in promoters. Most remarkably, methylation pattern of R508 treated p53$^{-/-}$ mice were very like both wt and Rlip$^{-/-}$ mice.
Hyper: Greater methylation in wt than the other sample; Hypo: Greater methylation in the other sample than in sample 1.

Rlip Regulates the Activity of Cancer-Signaling and Cytokine Pathways

Since Rlip is a rate determinant of CDE, a process that broadly regulates peptide hormone signaling, we compared the activity of several key cancer signaling pathways between control vs. R508-treated p53$^{-/-}$ mice. Activation or protein content of PI3K, AKT, mTOR, p70S6K, RB and BCL2 was reduced and that of HSF1, JNK, p27 (CDK1B) and BCL$_{XL}$ was increased in hepatic tissues of R508 treated mice. That this was a specific consequence of Rlip depletion was evident from similar effects of Rlip depletion in p53$^{-/-}$ MEF by shRNA on AKT, PI3K, CDK4, JNK, BCL2, BAX, mTOR, P70S6K, RB and p27. Furthermore, Rlip depletion modulated cytokine signaling down-stream of TNFα. Rlip depletion alone increased TNF-receptor protein 2 (TNFR2) and activated p38 preferentially in p53$^{-/-}$ MEF. Rlip depletion also lowered Rb phosphorylation in p53$^{-/-}$ MEFs and increased p19$^{ARF}$ (mouse homolog of human p14$^{ARF}$) levels independent of TNFα, a potential mechanism for inhibition of carcinogenesis. Through a series of studies to examine the role of Rlip in CDE, we confirmed its rate determining role in benign as well as malignant cells and showed for the first time that STAT3 signaling down-stream of FGF is regulated by Rlip.

Lymphoma Prevention by Rlip Depletion is Independent of Effects on Oxidative DNA Damage Since oxidative stress promotes carcinogenesis and can regulate DNA methylation, we considered the possibility that reduced oxidative DNA damage underlies cancer prevention. 4HNE level, a surrogate for overall oxidative stress, was ~8-fold higher in control p53$^{-/-}$ mice than in R508-treated mice, largely reflecting the presence of tissue damage. 4HNE level in R508 treated p53$^{-/-}$ mice were significantly lower than control p53$^{-/-}$ mice, like those in Rlip$^{-/-}$ mice but still significantly greater than wt as shown in FIG. 2A. Surprisingly, despite much lower oxidative stress, the levels of 8-OHdG (a measure of oxidative DNA damage) in R508-treated p53$^{-/-}$ mice were not significantly different than in the control p53$^{-/-}$ groups as shown in FIG. 2B. Potent prevention of malignancy without affecting oxidative DNA damage supports and existential requirement of Rlip for malignant transformation of genetically damaged cells: p53 loss served as the 'first-hit' and the presence of Rlip was the 'second hit' required for transformation.

Rlip, p53 and HSF1 Interactions

The abrupt switch in cancer susceptibility phenotype of p53$^{-/-}$ mice upon Rlip depletion to only a hemizygous level suggests a haploinsufficiency phenomenon, in which deficiency of a protein with multiple binding partners simultaneously alters the quantity and relative ratios of multiple heterodimers resulting in disproportionate phenotypic effects. HSF1 was an obvious candidate in haploinsufficiency interactions because HSF1 binds p53 during stress-induced nuclear translocation, Rlip regulates chaperone expression by inhibiting the nuclear translocation of HSF, and HSF1 deficiency alters the histological profile of malignancy in p53$^{-/-}$ mice. Because binding of p53 with HSF1 or with Rlip has been reported in ex-vivo and in-vitro but not in-vivo, we examined this possibility in present studies. Co-immunoprecipitation studies in wt, p53$^{+/-}$, and p53$^{-/-}$ MEFs demonstrated Rlip can specifically bind p53 and HSF1 as shown in FIG. 2C. PLA (proximity ligation assay) demonstrated cytosolic and nuclear interactions of p53 with Rlip in MEF as shown in FIG. 2D. Furthermore, PLA also demonstrated p53-Rlip and HSF1-p53 interactions in mouse liver as shown in FIG. 2E. Thus, the dramatic switch in cancer susceptibility of p53$^{-/-}$ by hemizygous Rlip deficiency is likely to be due to haploinsufficiency interactions between HSF1, p53 and Rlip.

Preventative and Therapeutic Implications of Targeting Rlip

Figure 3A:
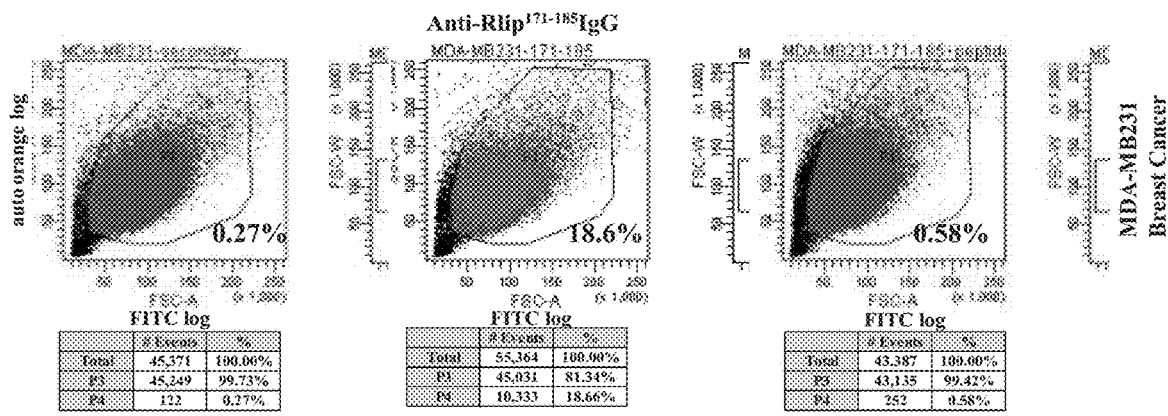
FIG. 3A shows the results from the determination of $Rlip^{171-185}$ peptide epitope on the surface of B16 melanoma cells by flow-cytometry using pre-immune antibody, anti-$Rlip^{171-185}$ antibody, and $Rlip^{171-185}$ peptide.
Figure 3B:
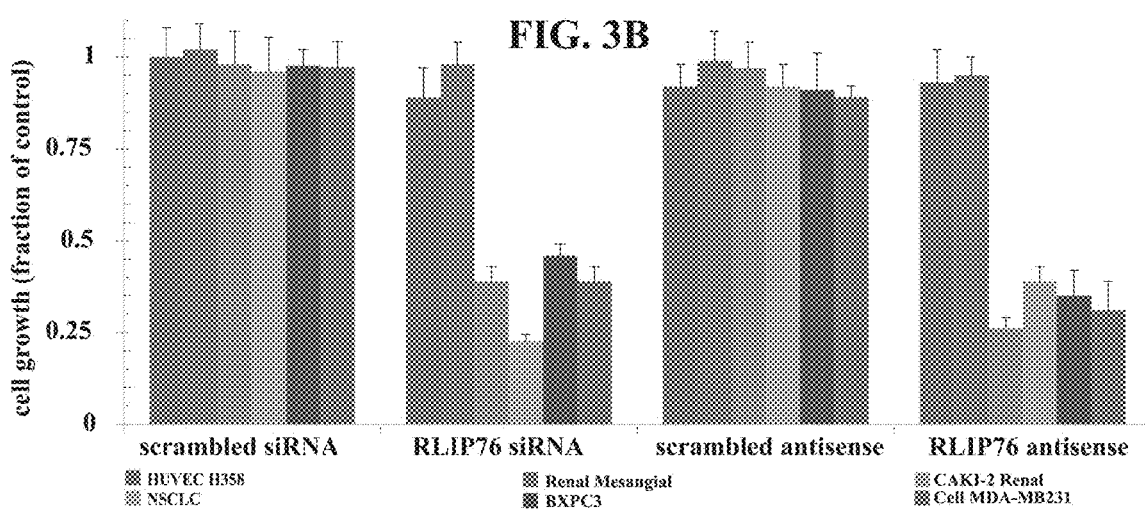
FIG. 3B shows the effect of Rlip depletion by R508 or Rlip-siRNA on cell growth inhibition determined by MTT assay.

Humanized monoclonal antibodies may be more pharmacologically suitable than antisense for treatment of p53-deficient malignancy or cancer prevention in Li-Fraumeni syndrome. Using polyclonal antibodies specific for the N$^{171-185}$ peptide and a cleavable biotinylation reagent (Sulfo-NHS-SS-Biotin) we observed the presence of the Rlip$^{171-185}$ epitope on the cell surface. This was confirmed by flow-cytometry on melanoma cells and the specificity of the cell surface detection was confirmed using competitive inhibition by the N$^{171-185}$ peptide as shown in FIG. 3A. These antibodies inhibited the growth of melanoma renal, lung, pancreas and breast cancer cells as effectively as antisense or siRNA as shown in FIG. 3B.

Discussion

Results of present studies showed that pharmacologically mediated partial suppression of Rlip protein prevented the appearance of lymphoma or any other malignancy in p53$^{-/-}$ mice. Normalization of the methylome and transcriptome of R508 treated mice strongly supported the results of gross, histological and immunohistochemical findings of the absence of any malignancy at necropsy. In-vivo studies showing diminished activation of key cell cycling, cell growth, replication checkpoint and cytokine signaling pathways at the protein level was also consistent with absence of malignancy in R508 treated mice. R508-induced hypoglycemia and hypolipidemia, and the overlap of transcriptomic effects of R508 treatment in p53$^{-/-}$ mice with Rlip knockout mice confirm target specificity, showing predicted pharmacodynamic endpoints that reflect Rlip deficiency. Finally, the cancer suppressive effect of Rlip deficiency in spontaneous and chemically induced malignancy models of mice with congenital deficiency of Rlip provide essentially incontrovertible evidence of specificity and rule our off-target effects in mechanisms of therapeutic actions of R508.

The pleiotropic involvement of p53 and Rlip in cancer-promoting biological processes, together with the global effects of Rlip deficiency on signaling, transcriptomic and epigenomic mechanisms that promote malignancy prevented determination of a specific mechanism of action for R508. Achievement of a near normal gene expression and DNA methylation profile in Rlip-deficient p53$^{-/-}$ mice and lack of malignancy in these mice despite high levels of oxidative stress indicates that p53 loss or oxidative stress are not the ultimate determinants of either epigenomic changes or malignant transformation. Rlip is an ATPase that catalyzes the efflux of pro-apoptotic electrophilic metabolites arising from lipid peroxidation and xenobiotic exposure. Potent anti-apoptotic function of Rlip have been established through development of recombinant Rlip protein as the most effective drug for treatment and prevention of radiation and chemical weapons poisoning. Thus, an existential requirement of its anti-apoptotic effect after malignant transformation could potentially explain lack of lymphoma in Rlip-deficient mice. Because Rlip regulates the rate of CDE and consequently the intensity of cancer-promoting signals down-stream of cell growth hormones, its deficiency could delay the appearance of lymphoma by slowing growth after malignant transformation. Cytokine signaling is regulated by CDE and promotes lymphoma growth. Rlip has been shown to be an effector in mitochondrial replication as well as in CDK1 functions during the cell-cycle, thus slowing cell growth or proliferation could be another mechanism that would delay the appearance of lymphoma. Rlip functions intersect with those of p53 at multiple levels including stress-response, drug/xenobiotic/radiation-resistance, transcriptional control of chaperones, apoptosis, and cell cycling. Regulation of CDE by p53 suggests another possible site of direct interaction. Thus, Rlip deficiency would affect multiple mechanisms that are also regulated by p53 and inhibit the survival and growth after malignant transformation. The question of whether Rlip deficiency acts after or prior to malignant transformation could not be directly answered, perhaps because it is semantic, depending on a precise definition of a developmental point at which transformation is clearly and irreversibly established.

Narrowing the key cancer promoting processes or the subset of genes whose expression is critical for lymphoma formation would have been possible by subtraction of expression profiles of R508 treated p53$^{-/-}$ with malignancy from aged p53$^{-/-}$ mice with altered transcriptomes but no malignancy; unfortunately, we observe no such cases. For the same reasons, our results cannot establish a cause-effect relationship between methylomic aberrations and lymphomagenesis in p53$^{-/-}$ mice or between correction of methylomic aberrations and lymphoma suppression by R508-treatment. However, a nearly normal methylome in cancer-free R508-treated p53$^{-/-}$ mice despite persistent extensive oxidative DNA damage clearly shows that methylomic aberrations are not an obligatory consequence of either p53 deficiency or oxidative DNA damage in the setting of partial Rlip deficiency. Interestingly, we found <50 DMRs between Rlip$^{-/-}$ vs. wt mice (data not presented), ruling out any direct role of Rlip in enzymatic mechanisms that catalyze DNA methylation or de-methylation. The absence of an Rlip-p53 heterodimer in both Rlip$^{-/-}$ and the p53$^{-/-}$ mice, by definition, also rules out any direct role of such a heterodimer in mechanisms of DNA-methylation. By the same reasoning, the opposite cancer susceptibility phenotype of Rlip$^{-/-}$ and p53$^{-/-}$ mice can also not be explained by a direct effect of such a heterodimer. Thus, additional factors are believed to operate through haploinsufficiency mechanisms.

HSF1 interacts with both p53 and Rlip. The HSF1-p53 complex translocates to the nucleus in response to stress. HSF1 loss in p53$^{-/-}$ mice switches the cancer phenotype, from primarily lymphoma to primarily adenocarcinoma or sarcoma without altering the overall incidence of malignancy. Rlip inhibits chaperone transcription by sequestering HSF1 in a tubulin-bound complex that dissociates upon stress exposure, releasing HSF1 for nuclear translocation. Consistent with this, numerous chaperones are upregulated in Rlip$^{-/-}$ mice. A mutually inhibitory relationship is evident from inhibition of transport and anti-apoptotic activities of Rlip by HSF1. The Rlip-p53 interactions were indicated by inhibition of the transport activity of Rlip by p53 and reduced binding of Rlip to mutant p53 in neuroblastoma cells. Present studies show an Rlip-p53 complex exists in-vitro and in-vivo. The three proteins are believed to coordinately regulate transcriptional responses to stress, while Rlip serves as an anti-apoptotic effector and feedback inhibitor of p53 and HSF1. Only the p53-HSF1 dimer can exist in the absence of Rlip, which is believed to prevent cancer and only the Rlip-HSF1 can exist in the absence of p53, which is believed to promote cancer. There are numerous other examples of haploinsufficiency interactions that cause abrupt changes cancer susceptibility of p53$^{-/-}$ mice. However, none of these result in the dramatic phenotypic switch from universal cancer susceptibility to nearly complete resistance to spontaneous as well as chemically induced carcinogenesis as observed in present studies.

In conclusion, our studies establish a strong dominant negative effect of Rlip-deficiency on the cancer susceptibility phenotype conferred by Rlip loss and support an existential need of Rlip for cancer formation in the mouse model. A new paradigm for defining the role of p53 in carcinogenesis and epigenetics is disclosed herein. The methods disclosed herein can be applied to broad cancer prevention as well as therapy because of abnormal p53 function in most human cancers. Further disclosed is a method of using chronic partial Rlip deficiency to prevent or treat malignancy in individuals with Li-Fraumeni syndrome. Because targeted depletion of Rlip causes regression of malignancy in pre-clinical models regardless of the p53 status of the neoplasm, the methods disclosed herein are believed to exert a very broad-spectrum therapeutic effect.

The potent anti-apoptotic and stress-defense functions of Rlip indicate application in drug- or radiation-resistant malignancy. Because only a hemizygous state of Rlip deficiency is needed, the likelihood of adverse effects is mitigated. Indeed, collateral health benefit could also be realized through reduction of blood glucose, insulin-resistance, and hyperlipidemia.

EXAMPLES

Example 1

Rlip Deficiency Prevents Carcinogenesis and Reverts Transcriptomic and Methylomic Abnormalities in p53 Knockout Mice Treatment of p53–/– Mice with R508 Phosphorothioate Antisense Oligonucleotide Animal experiments were performed under approved IACUC protocol #11016 on eight-week old male C57BL/6J p53$^{-/-}$ mice on a B6.129S2-Trp53$^{tm1Tyj}$/J background purchased from Jackson Laboratory (Bar Harbor, Me.). Mice with homozygous knockout of RALBP1 (referred to here as Rlip$^{+/-}$) were generated by Lexicon genetics (The Woodlands, Tex.), and mice born of Rlip$^{+/-}$ × Rlip$^{+/-}$ mating, were genotyped by PCR strategy as described previously by Awasthi et al. in Cancer Res. 2005; 65: 6022-6028. R508 is based on the unique Rlip gene nucleotide sequence $^{508}$GGCTCCTGAATTGGCTTTTTC$^{529}$ SEQ ID NO.: 1 with least homology to nucleotide sequences in the human or mouse genome. Control scrambled phosphorothioate oligonucleotide (CAS) sequence, generated using GenScript software was CATCGAAATCGTTGCAGTTAC SEQ ID NO.: 7. CAS does not deplete Rlip or cause apoptosis, xenograft regression, hypoglycemia, hypolipidemia, or insulin sensitivity. R508 or CAS were dissolved in PBS (1 mg/mL) and 0.2 mL was administered weekly for 24 weeks by i.p. injection starting at 8 week age.

Spontaneous and Chemical Carcinogenesis in p53 and Rlip Knockout Mice

Cross breeding of p53$^{+/-}$ C57B16 mice with Rlip$^{+/-}$ was performed to obtain colonies of mice with the genotypes: p53$^{-/-}$Rlip$^{+/+}$, p53$^{-/-}$Rlip$^{+/-}$, p53$^{-/-}$Rlip$^{-/-}$, and p53$^{+/-}$Rlip$^{+/-}$. For spontaneous carcinogenesis, mice were monitored 3 times per week for distress or overt malignancy and all surviving mice were euthanized at age 48 wk. Chemical carcinogenesis was studied in mice administered 3 mg B[a]P in 1 mL corn-oil by gavage at the age of 8 and 12 weeks.

Cell Culture

MEF were derived and maintained in culture at 12 to 13-day gestation by previously described methods by Singhal et al. in Int J Radiat Oncol Biol Phys. 2008; 72:553-561. p53$^{-/-}$ MEFs were provided by Dr. Arnold J. Levine, Cancer Institute of New Jersey/UMDNJ, New Brunswick, N.J. All malignant cell lines were purchased from ATCC except for the mouse Raji and human LCL lymphoma cell lines, which were a gift from Prof. Stephen J. Forman, City of Hope, Duarte, Calif. Mycoplasma testing was done using Universal Mycoplasma Detection kit. Malignant cells were grown in RPMI1640 medium and MEFs in DMEM containing 10% FBS and 1% penicillin/streptomycin at 37° C. in 5% $CO_2$. Cytotoxicity, signaling, and endocytosis studies were performed in serum free medium after washing cells in Hanks' PBS.

Histological and Immunohistochemical Analyses

Tissues were fixed with formalin-B5 fixative and 5 µm thick histological sections were stained with hematoxylin/ eosin by standard methods in the City of Hope Animal Pathology Core facilities. Universal ABC detection kit was purchased from Vector (Burlingame, Calif.). Primary antibodies and secondary horseradish peroxidase antibodies used in immunohistochemistry (IHC) were purchased from Abcam Inc. (Cambridge, Mass.). Light microscopy was performed using an Olympus Provis AX70 microscope interfaced with a Nikon camera and ImagePro software by a veterinary pathologist blinded to treatment groups.

Western Blot Analyses of Signaling Proteins

Western blotting was performed by standard methods using the Chemiluminescence ECL kit with a horseradish peroxidase conjugated anti-IgG secondary antibody (Amersham Life Sciences). Sources of primary antibodies are indicated in figure descriptions. GAPDH and β-acting were loading controls. Densitometry was performed using Alpha Imager HP. Rlip shRNA pSR/puro/Ralbpl (plasmid 31115) and scrambled shRNA (plasmid 1864) used to deplete Rlip to examine the effects on signaling proteins in cultured MEFs were purchased from Addgene (Cambridge, Mass.). Invitrogen Lipofectamine 2000 purchased from Thermo Fisher Scientific (Waltham, Mass.) was used for shRNA plasmid transfection and cells were lysed with cell lysis buffer from Cell Signal Technology (Danvers, Mass.).

RNA-Seq Studies and Validation of Results by qRT-PCR

RNA samples were prepared using the RNeasy mini kit from Qiagen (Valencia, Calif) according to manufacturer instructions. RNA quality was assessed by microfluidic capillary electrophoresis using an Agilent 2100 Bioanalyzer. The RNA 6000 Nano Chip kit from Agilent Technologies (Santa Clara, Calif.) was used for subsequent library preparation. Sequencing libraries were prepared with the TruSeq RNA Sample Prep Kit V2 from Illumina (San Diego, Calif.) according to the manufacturer's protocol. Removal of ribosomal RNA was carried out from 500 ng total RNA using the RiboZero kit from Illumina and resulting RNA ethanol precipitated. First-strand cDNA synthesis was performed using DNA polymerase I and RNase H. cDNA was end repaired, and 3' end adenylated. Universal adapters were ligated followed by 10 cycles of PCR using Illumina PCR Primer Cocktail and Phusion DNA polymerase from Illumina. Subsequent library purification with Agencourt AMPure XP beads was validated with Agilent Bioanalyzer 2100, and quantified with Life Technologies' Qubit purchased from ThermoFisher (Waltham, Mass.). Sequencing was conducted on Illumina HiSeq 2500 with single end 50 bp reads. Reads were aligned using Tophat v2.0 to mouse reference genome mm9. Expression level of RefSeq genes were counted and normalized using TMM method and differential expression analysis was conducted using a linear model based on negative binomial distribution using "edgeR". RPKM (reads per kilobase per million mapped reads)=# of reads/(gene length/1000*total number of reads/1,000,000). Analyses were performed by censoring the lowest expressed genes or using $\log_2(RPKM+0.1)$ expression levels. To satisfy the criteria for differential expression, a p value<=0.01, fold change>=2, and RPKM>=1 in at least 2 samples was required. RNA-Seq results were confirmed using real-time quantitative PCR. cDNA using gene primers was performed on an ABI-7500 fast real-time PCR system using SYBR Green master mix. 1 µg of total RNA from liver was used to synthesize cDNA by reverse transcription using the RT kit (Applied Biosystems). To validate RNA-Seq results, qRT-PCR was conducted with primers purchased pre-validated from BioRad (PrimePCR, cat. 10025636) for the following genes: Cib3, Dlk1, Cyp4a32, Fzd10, Gpr3, Tff1, and Six3. The internal control primer sequences for ZZZ3 were AGACCATTGCTGTACTTGAGG SEQ ID NO.: 8 and GGTATGGAAGCCCTATGTCAG SEQ ID NO.: 9. Reactions were conducted in triplicate for each biological replicate and data is expressed as $\log_2$ fold change in $p53^{-/-}$ CAS or R508 treated mice relative to wild-type using the comparative Ct method. RNA-Seq data was normalized using the above internal reference genes and linear regression was used to determine correlation between RNA-Seq and qRT-PCR data. GO pathway terms were ranked by p-value (EASE score).

Whole-Genome Bisulfite Sequencing and Reduced Representation Bisulfite Sequencing (RRBS)

The amount of input material for the BS-Seq libraries was between 5 ng and 20 ng genomic DNA. The input DNA was sonicated, and end repair and A-tailing were performed using the NEB Next kit according to the manufacturers' instructions. Illumina's Early Access Methylation Adaptor Oligo Kit was used for the adaptor ligation. The adaptor-ligated DNA was treated with sodium-bisulfite using the Imprint DNA Modification Kit from Invitrogen according to the manufacturer's instructions for the two-step protocol. Bisulfite-treated DNA was amplified using PfuTurbo Cx Hotstart DNA Polymerase from Agilent Technologies with 14-18 cycles depending on the input amount. Size selection was performed by gel extraction for DNA fragments between 200 bp and 250 bp. The resulting library was sequenced on an Illumina HiSeq 2000 sequencer, with image analysis and base calling done using the default RTA analysis software. Reads were aligned to in silico bisulfite converted mm9 genome using Bismark aligner (CITE) using default settings. The methylation level of each CpG site was calculated as the number of non-converted cytosine divided by the sum of converted and non-converted cytosine. CpG sites with less than 3× coverage were excluded. Methylated regions were defined as those with ≥5 pairs of CpG sites merged if they were <200-bp apart. Those with p ≤0.05 and average difference ≥0.25 were considered significant. To determine the methylation levels of CpG sites within promoters, we used the RefSeq gene's promoter region (defined as ±1000 bp of transcription start site) to calculate average promoter methylation level. Promoters having at least one sample with >50% methylation level and range of methylation level across the four samples >25% were selected for analyses. To identify the regions that were hyper-methylated in sample A vs. B (differential methylated regions), the regions had to satisfy three criteria: 1) methylation level in sample A was >60%; 2) methylation level in sample B was <50%; and 3) the methylation difference was >45%. DMRs were annotated using the mm9 RefSeq database. Regions between 1 kb from transcription start site to transcription end site were categorized as "gene body"; regions not overlapping with above regions were categorized as "intergenic".

Quantitative validation was carried out for the PTPN6 and HOXA5 gene promoters by conventional bisulfite sequencing. Bisulfite conversion of genomic DNA was performed with EpiTect Bisulfite Kit (Qiagen). Primers were designed with MethPrimer software using genomic coordinates of identified regions of differential methylation (140). The forward/reverse primer sequences were as follows: PTPN6-ATTTAAGGTGGATGATGGTGTTATT SEQ ID NO.: 10/TCCAAAACTCAAAAAACTTCTATAACC SEQ ID NO.: 11; HOXA5—GTTTGATGATTTT-TAGAGGTAAATT SEQ ID NO.: 12/CCATAATAAAC-TATAACCTCAATTC SEQ ID NO.:13; corresponding annealing temperatures were 53 and 52° C. Bisulfite PCR-amplified DNA was separated using 2% agarose gel electrophoresis and bands extracted with a Gel Extraction Kit (Qiagen). Purified target DNA was cloned into pDrive vector and EZ competent cells were transformed with plasmid DNA (PCR Cloning plus Kit; Qiagen). DNA was isolated from transformed bacteria (Qiaprep Spin Miniprep; Qiagen) and sequenced at City of Hope DNA sequencing core. Finally, DNA methylated sequence analysis was conducted with Bisulfite Sequencing DNA Methylation Analysis Software v9 (BISMA).

8-hydroxy-deoxyguanosine and 4-hydroxynonenal Measurements

ELISA assay kits (Cell Biolabs, San Diego, Calif.) were used to measure 8-hydroxydeoxyguanosine (8OHdG) and 4-hydroxynonenal (4HNE). A 96-well plate ELISA assay was used with spectrophotometric detection using a Tecan Pro200 plate reader at 450 nm. Analyte concentrations were estimated from standard curves generated from standards provided in the respective kits.

Studies of HSF1, Rlip and p53 Protein-Protein Interactions

Binding interactions of HSF1, Rlip and p53 in wt, p53$^{-/-}$ MEFs without or with Rlip depletion using R508 were studied by co-immunoprecipitation using protein A/G PLUS-Agarose immunoprecipitation reagent sc-2003 from Santa Cruz Biotechnology (Columbus, Ohio) according to the manufacture's protocol using whole-cell homogenates of wild-type, p53$^{-/-}$ or p53$^{+/-}$ MEFs. Primary anti-HSF1 rabbit monoclonal antibody (D3L8I) and anti-p53 mouse monoclonal antibody was from Cell Signaling Technology (Danvers, Mass.), and rabbit monoclonal anti-Rlip antibody was from Abcam (Cambridge, Mass.). The specificity of primary antibodies was tested using MEFs from either p53$^{-/-}$ or Rlip$^{-/-}$ MEFs. The corresponding probes of anti-rabbit PLUS and anti-mouse MINUS were provided in the kit and used per the manufacturer's instructions. wt, p53$^{-/-}$ and p53$^{-/-}$ MEFs were used. The Duolink® in-situ orange mouse/rabbit proximity ligation assay (PLA) from Sigma (St. Louis, Mo.) was used to study Rlip, p53 and HSF1 interactions in cultured MEF and mouse liver tissue sections per the manufacturer's instructions. For technical controls, we omitted one of the two primary antibodies. Purified polyclonal rabbit or mouse pre-immune IgG fractions were used as additional controls during assay optimization. Slides were visualized by fluorescence microscopy using an Olympus BX50 microscope, and photomicrographs were taken using a 40× objective.

Statistical Analyses

Statistical methods used for RNA-Seq, WGBS and expression array analyses are given above. Results for both types of studies were analyzed for effects on genes, pathways and processes using Integrated Pathways Analysis (IPA, Qiagen Inc.) and DAVIDv6.7 (Database for Annotation, Visualization and Integrated Discovery). GOTERM_BP_FAT, GOTERM_CC_FAT GOTERM_MF_FAT, and KEGG_PATHWAY databases were included. Enriched ontology terms had to have >4 genes and an EASE score <0.05. Ontology results from each database were ranked by p-value. For analyses of DMRs lists, the genomic region had to exceed >100 identifiers. For other studies, experimental group comparisons were performed using two-tailed unpaired student's t test are expressed as the mean±SD. The statistical significance of differences between control and treatment groups was determined by ANOVA followed by Bonferroni correction and Benjamin-Hochberg procedure with false discovery rate <0.05. The heat map of the p-values of top differentially expressed genes by Euclidean distance and an average linkage strategy for the four groups (wt, PBS-p53-/-, CAS-p53-/- and R508-p53-/-) are obtained. Changes in tumor size and body weight during the experiments were visualized by scatter plot. Differences were considered statistically significant if p<0.05.

Figure 1G:
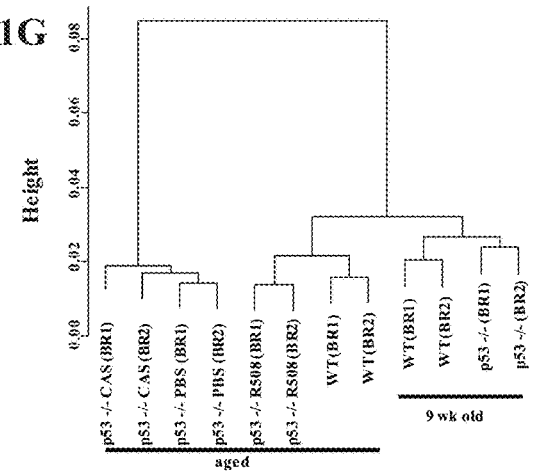
FIG. 1G shows Java Tree view of promoters hierarchical clustering of PBS, CAS, or R508-treated p53−/− mice, young (9 week) wt or p53−/− mice, and aged wt mice.

Veterinary pathologists performed complete gross and histological necropsy on all euthanized mice. Tumor free-survival curve is shown in FIG. 1A for mice treated weekly with i.p. injection of 0.2 mL PBS containing CAS or R508 (0.2 mg each) for up to 24 weeks. All surviving animals were euthanized at 32-week age. Overall survival curves for double-knockout mice of the indicated genotype are shown in FIG. 1B. No treatment was given and the mice were euthanized if there was appearance of morbidity. All surviving mice were euthanized at 48-week age. Mice of the indicated genotypes were administered 3 mg benzo[a]pyrene in corn oil by gavage at age 8-week and 12-week and the results shown in FIG. 1C. All mice euthanized during the study because of appearance of morbidity as well as those euthanized at the end of the study at 24-weeks underwent necropsy to determine the incidence of cancer (lung+gastric). The heat map show in FIG. 1D uses scale-standardized expression to show hierarchical clustering of RNA-Seq samples by correlation with centroid linkage, gene ordering by cluster tightness. For inclusion in clustering a gene had to be expressed at >10 log$_2$ RPKM in any one sample. WGBS (BS-Seq) was performed on liver tissues and the results shown in FIG. 1E. Young (9-week) wt and p53-/- mice were aging controls. The aged (32 week) wt mice were cancer-free controls for the R508-treated 53$^{-/-}$ mice and the aged (18-24 week) PBS or CAS-treated p53-/- mice were controls for R508-treatment. Conventional bisulfite sequencing was used to validate WGBS results and the WGBS results (black bars) were aligned with RNA-Seq (transcriptomic) results (red bars), shown with exons and introns (bottom line). CBS on the promoter region (gray box) are shown in the grid on the right, with black dots indicating methylated and white dots indicating un-methylated sites within the PTPN6 gene promoter. The height of the bars represent degree of methylation and height of the red bars is proportional to mRNA expression. Total CpG island methylation compared between PBS, CAS, or R508-treated p53-/- mice, young (9 week) wt or p53-/- mice, and aged wt mice by Pearson's dissimilarity matrix is show in FIG. 1F. BR1/2 stand for biological replicates. Promoters defined using RefSeq (+/−1000 bp of transcription start site) were selected if average CpG site methylation level was >50% in at least one sample and methylation range was >25%. Hierarchical clustering was performed using average linkage algorithm and visualized by Java Treeview and the results shown in FIG. 1G.

Example 2

Effect of R508 on Oxidative Stress Damage and Stress-Responses

The 4-hydroxynonenal (4HNE) and 8-OH-deoxyguanosine (8OHdG) levels were measured in liver homogenate using Oxiselect kits from Cell Biolabs, San Diego, Calif. by procedures described in Methods and the results are shown in FIG. 2A and FIG. 2B, respectively. Analyte concentrations were estimated using standards provided in the respective kits. Co-immunoprecipitation studies were carried out in whole cell homogenates of wt and p53 knockout MEFs without or with treatment with R508 and the results are shown in FIG. 2C with immunoprecipitating antibody shown above the blot. The antibody used for Western blot is shown on the left. Interactions between Rlip, p53 and HSF1 in wt MEF were studied by proximity ligation assays (PLA, Duolink® In Situ Orange Starter Kit Mouse/Rabbit, Sigma, St. Louis Mo.) in cultured wt MEFs and 5 μm liver tissue sections. The results from cultured wt MEFs is shown in FIG. 2D and the results from 5 μm liver tissue sections are shown in FIG. 2E. Primary anti-HSF1 rabbit monoclonal antibody (D3L8I) and anti-p53 mouse monoclonal antibody was from Cell Signaling Technology (Danvers, Mass.) and rabbit monoclonal anti-Rlip antibody was from Abcam (Cambridge, Mass.). The corresponding probes for PLA were anti-rabbit PLUS and anti-mouse MINUS antibody probes provided in the kit and used according to the manufacturer's instructions. In FIG. 2D Rlip antibody was omitted in the control shown for MEF studies; additional controls, where either p53 antibody or secondary antibody were omitted, are not shown. In the control with p53 antibody omitted is shown for tissue studies; additional controls are not shown. Results of interaction of HSF1 with p53 and Rlip with p53 in mouse liver tissue are shown in FIG. 2E. Slides were visualized by fluorescence microscopy using an Olympus BX50 microscope (40× objective)

Example 3

Anticancer Effects of Targeting Rlip by Antibodies

Figure 3C:
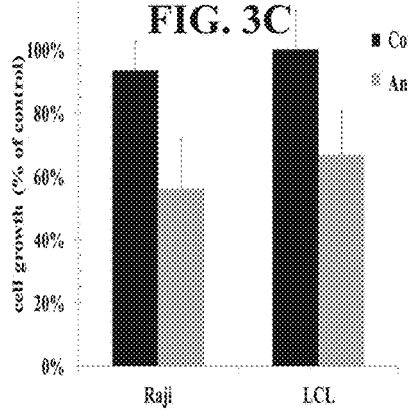
FIG. 3C shows growth inhibition of Raji and LCL lymphoma cell lines by anti-$Rlip^{171-185}$ antibody (20 μg/mL) determined by MTT assay.
Figure 3D:
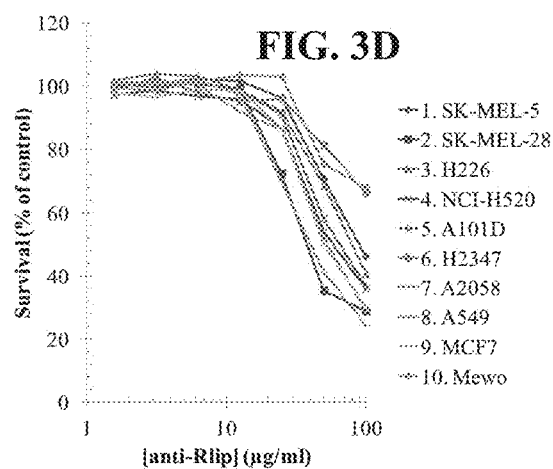
FIG. 3D shows growth inhibition curves of the concentration dependent effects of the anti-$Rlip^{171-185}$ antibody against multiple malignant cell lines.

Presence of the Rlip$^{171-185}$ peptide epitope on the surface of the B16 melanoma cells was determine by flow-cytometry using pre-immune antibody, anti-Rlip$^{171-185}$ antibody, and by including the Rlip$^{171-185}$ peptide with anti-Rlip$^{171-185}$ antibody to competitively inhibit specific binding as shown in FIG. 3A. The percentage of cells displaying cell surface fluorescence is given in each panel. Effect of Rlip depletion by R508 or Rlip-siRNA on cell growth inhibition was determined by MTT assay at 48 h after transfection with lipofectamine and the results shown in FIG. 3B. CAS and control scrambled siRNA with the same sequence served as controls. The non-malignant transformed cell lines were human umbilical vein endothelial cell (HUVEC) and renal mesangial. The malignant cell lines were CAKI-2 renal cell carcinoma, H358 human lung bronchioalveolar non-small cell carcinoma, BXPC3 pancreatic carcinoma and MDA-MB-231 ER/PR/Her2 negative breast carcinoma. Growth inhibition of Raji and LCL lymphoma cell lines by anti-Rlip$^{171-185}$ antibody (20 μg/mL) was measured using an MTT assay and the results shown in FIG. 3C. The control consisted of antibody heat-inactivated by incubation for 2 min at 70° C. Growth inhibition curves showing the concentration dependent effects of the anti-Rlip$^{171-185}$ antibody against multiple malignant cell lines: melanoma, (SK-MEL-5, SL-MEL-28, A101D, A2058 and MeWo), human NSCLC (H226, H520, H2347, and A549) and human breast (MCF7) is shown in FIG. 3D. Results are from one of three experiments, with 8 technical replicates.

The selected siRNA sequence was blast-search (NCBI database) against EST libraries, to ensure that only one gene is targeted. Chemically synthesized siRNA duplex in the 2' de-protected and desalted forms, was purchased from Dharmacon Research (Lafayette, Colo.). A 23 nucleotide long scrambled siRNA duplex was used as a control. The scrambled siRNA sequence was not homologous with RLIP76 mRNA in a blast-search against RLIP76. The siRNA duplex was re-suspended in 1× universal buffer, provided by Dharmacon Research Laboratory. The targeted cDNA sequence (AAGAAAAAGCCAATTCAGGAGCC SEQ ID NO.: 5) corresponds to aa 170-176 (nt 508-528). The corresponding sense and antisense siRNA sequences are GAAAAAGCCAAUUCAGGAGCCdTdT SEQ ID NO.: 3 and GGCUCCUGAAUUGGCUUUUUCdTdT SEQ ID NO.: 6, respectively. The sequence of the scrambled siRNA in the sense and antisense directions are GUAACUGCAACGAUUUCGAUGdTdT SEQ ID NO.: 14 and CAUCGAAAUCGUUGCAGUUACdTdT SEQ ID NO.: 15, respectively. Transfection of siRNA duplexes was performed using Transmessenger Transfection Reagent kit (Qiagen) and assay for silencing 24 h after transfection.

REFERENCES

1. Lane D P. Cancer. p53, guardian of the genome. Nature. 1992 Jul. 2; 358(6381):15-6.
2. Levine A J, Oren M. The first 30 years of p53: growing ever more complex. Nat. Rev. Cancer 2009; 9:749-758.
3. Zilfou J T, Lowe S W. Tumor Suppressive Functions of p53. Cold Spring Harb Perspect Biol. 2009 November; 1(5): a001883.
4. Donehower L A, Lozano G. 20 years studying p53 functions in genetically engineered mice. Nat. Rev. Cancer. 2009; 9:831-841
5. Ariffin H, Hainaut P, Puzio-Kuter A, Choong S S, Chan A S, Tolkunov D, Rajagopal G, Kang W, Lim L L, Krishnan S, Chen K S, Achatz M I, Karsa M, Shamsani J, Levine A J, Chan C S. Whole-genome sequencing analysis of phenotypic heterogeneity and anticipation in Li-Fraumeni cancer predisposition syndrome. Proc Natl Acad Sci USA. 2014 Oct. 28; 111(43):15497-501.
6. Villani A, Tabori U, Schiffman J, Shlien A, Beyene J, Druker H, Novokmet A, Finlay J, and Malkin D. Biochemical and imaging surveillance in germline TP53 mutation carriers with Li-Fraumeni syndrome: a prospective observational study. Lancet Oncol. 2011; 12, 559-567
7. Nantasanti S, Toussaint M J, Youssef S A, Tooten P C, de Bruin A. Rb and p53 liver functions are essential for xenobiotic metabolism and tumor suppression. PLoS One. 2016 Mar. 11; 11(3): e0150064.
8. Sablina A A, Budanov A V, Ilyinskaya G V, Agapova L S, Kravchenko J E, Chumakov P M. The antioxidant function of the p53 tumor suppressor. Nat Med. 2005 Dec; 11(12):1306-13.
9. Shetzer Y, Solomon H, Koifman G, Molchadsky A, Horesh S, Rotter V. The paradigm of mutant p53-expressing cancer stem cells and drug resistance. Carcinogenesis. 2014 June; 35(6):1196-208.
10. Awasthi S, Singhal S S, Srivastava S K, Zimniak P, Bajpai K K, Saxena M, Sharma R, Ziller S A III, Frenkel E, Singh S V, He N-G, Awasthi Y C. ATP-dependent transport of doxorubicin, daunomycin and vinblastine in human tissues by a mechanism distinct from the P-glycoprotein. J Clin Invest. 1994; 93:958-965.
11. Awasthi S, Singhal S S, Srivastava S K, Torman R T, Zimniak P, Bandorowicz-Pikula J, Singh S V, Piper J T, Awasthi Y C, Pikula S. ATP-dependent human erythrocyte glutathione-conjugate transporter. I. Purification, photoaffinity labeling and kinetic characteristics of ATPase activity. Biochemistry. 1998; 37: 5231-5238.
12. Awasthi S, Singhal S S, Pikula S, Piper J T, Srivastava S K, Torman R T, Bandorowicz-Pikula J, Lin J T, Singh S V, Zimniak P, Awasthi Y C. ATP-dependent human erythrocyte glutathione-conjugate transporter. II. Functional reconstitution of transport activity. Biochemistry. 1998; 37: 5239-5248.
13. Awasthi S, Cheng J, Singhal S S, Saini M K, Pandya U, Pikula S, Pikula J, Singh S V, Zimniak P, Awasthi Y C. Novel function of human RLIP76: ATP-dependent transport of glutathione-conjugates and doxorubicin. Biochemistry. 2000; 39:9327-9334.

14. Awasthi S, Cheng J, Singhal S S, Sharma R, Pandya U, Zimniak P, Awasthi Y C. Functional reassembly of xenobiotic transport from the N-terminal and C-terminal domains of RLIP76 and identification of ATP binding sequences. Biochemistry. 2001; 40: 4159-4168.
15. Sharma R, Singhal S S, Wickramarachchi D, Awasthi Y C, Awasthi S. RLIP76 (RALBP1) mediated transport of leukotrienes C4 (LTC4) in cancer cells: Implications in drug resistance. Int J Cancer, 2004; 112: 934-942.
16. Cheng J, Sharma R, Yang Y, Singhal S S, Sharma A, Saini M K, Singh S V, Zimniak P, Awasthi S, Awasthi Y C. Accelerated metabolism and exclusion of 4-hydroxynonenal through induction of RLIP76 and hGST5.8 is an early adaptive response of cells to heat and oxidative stress. J Biol Chem. 2001; 276: 41213-41223.
17. Yang Y, Sharma A, Sharma R, Patrick B, Singhal S S, Zimniak P, Awasthi S, Awasthi Y C. Cells preconditioned with mild, transient UVA irradiation acquire resistance to oxidative stress and UVA-induced apoptosis: Role of 4-hydroxynonenal in UVA mediated signaling for apoptosis. J Biol Chem. 2003; 278: 41380-41388.
18. Yadav S, Singhal S S, Singhal J, Wickramarachchi D, Knutson E, Albrecht T B, Awasthi Y C, Awasthi S. Identification of Membrane Anchoring domains of RLIP76 using deletion mutant analyses. Biochemistry. 2004; 43: 16243-16253.
19. Awasthi S, Singhal S S, Yadav S, Singhal J, Drake K, Nadkar A, Zajac E, Wickramarachchi D, Rowe N, Yacoub A, Boor P, Dwivedi S, Dent P, Jarman W, John B, Awasthi Y C. RALBP1 is a major determinant of radiation sensitivity. Cancer Res. 2005; 65: 6022-6028.
20. Stuckler D, Singhal J, Singhal S S, Yadav S, Awasthi Y C, Awasthi S. RLIP76 Transports vinorelbine and mediates drug resistance in non-small cell lung cancer. Cancer Res. 2005; 65: 991-998.
21. Singhal S S, Awasthi Y C, Awasthi S. Regression of melanoma in a murine model by RLIP76 depletion. Cancer Res. 2006; 66: 2354-2360.
22. Singhal J, Singhal S S, Yadav S, Suzuki S, Warnke M M, Yacoub A, Dent P, Bae S, Sharma R, Awasthi Y C, Armstrong D W, and Awasthi S. RLIP76 in defense of radiation poisoning. Int J Radiat Oncol Biol Phys. 2008; 72:553-561.
23. Singhal S S, Singhal J, Yadav S, Dwivedi S, Boor P J, Awasthi Y C, Awasthi S. Regression of lung and colon cancer xenografts by depleting or inhibiting RLIP76 (Ral-binding protein 1. Cancer Res. 2007; 67:4382-9.
24. Singhal S S, Yadav S, Drake K, Singhal J, Awasthi S. Hsf1 and POB1 induce drug-sensitivity and apoptosis by inhibiting Ralbp1. J Biol Chem. 2008; 83:19741-29.
25. Singhal S S, Yadav S, Singhal J, Sahu M, Awasthi Y C, Awasthi S. RLIP76: A target for kidney cancer therapy. Cancer Res 2009; 69:4244-51.
26. Singhal S S, Roth C, Leake K, Singhal J, Yadav S, Awasthi S. Regression of prostate cancer xenografts by RLIP76 depletion. Biochem Pharmacol. 2009; 77(6): 1074-83.
27. Singhal S S, Sherawat A, Sahu M, Singhal P, Vatsyayan R, Lelsani P C, Yadav S, Awasthi S. RLIP76 transports sunitinib and sorafenib and mediates drug resistance in kidney cancer. Int J Cancer. 2010 Mar. 15; 126(6):1327-38.
28. Singhal S S, Wickramarachchi D, Yadav S, Leake K, Vatsyayan R, Lelsani P, Chaudhary P, Suzuki S, Awasthi Y C, Awasthi S. Glutathione-Conjugate Transport by RLIP76 is required for Clathrin-Dependent Endocytosis and Chemical Carcinogenesis. Mol Cancer Ther. 2011; 10(1):16-28.
29. Singhal J, Yadav S, Nagaprashantha L D, Vatsyayan R, Singhal S S, Awasthi S. Targeting p53-null neuroblastomas through RLIP76. Cancer Prev Res (Phila.). 2011 June; 4(6):879-89.
30. Leake K, Singhal J, Nagaprashantha L D, Awasthi S, Singhal S S. RLIP76 regulates PI3K/Akt signaling and chemo-radiotherapy resistance in pancreatic cancer. PLoS One. 2012; 7(4):e34582.
31. Awasthi S, Singhal S S, Yadav S, Singhal J, Vatsyayan R, Zajac E, Luchowski R, Borvak J, Gryczynski K, Awasthi Y C. A central role of RLIP76 in regulation of glycemic control. Diabetes. 2010 March; 59(3):714-725.
32. Singhal J, Nagaprashantha L, Vatsyayan R, Awasthi S, Singhal S S. RLIP76, a glutathione-conjugate transporter, plays a major role in the pathogenesis of metabolic syndrome. PLoS One. 2011; 6(9): e24688.
33. Singhal S S, Figarola J, Singhal J, Reddy M A, Liu X, Berz D, Natarajan R, Awasthi S. RLIP76 protein knockdown attenuates obesity due to a high-fat diet. J Biol Chem. 2013; 288:23394-406.
34. Brown M S, Goldstein J L. Receptor-mediated endocytosis: insights from the lipoprotein receptor system. Proc Natl Acad Sci USA. 1979 July; 76(7):3330-7.
35. Sorkin A, Zastrow M. Endocytosis and signaling: intertwining molecular networks. Nat Rev Mol Cell Biol. 2009 September; 10(9):609-622.
36. Tsujimoto M, Yip Y K, Vilcek J. Tumor necrosis factor: specific binding and internalization in sensitive and resistant cells. Proc Natl Acad Sci USA. 1985 November; 82(22):7626-30.
37. Pinilla-Macua I, Sorkin A. Methods to study endocytic trafficking of the EGF receptor. Methods Cell Biol. 2015; 130:347-67.
38. Jean S, Mikryukov A, Tremblay M G, Baril J, Guillou F, Bellenfant S, Moss T. Extended-synaptotagmin-2 mediates FGF receptor endocytosis and ERK activation in vivo. Dev Cell. 2010 Sep 14; 19(3):426-39.
39. Jullien-Flores V, Dorseuil O, Romero F, Letourneur F, Saragosti S, Berger R, Tavitian A, Gacon G, Camonis J H. Bridging Ral GTPase to Rho pathways. RLIP76, a Ral effector with CDC42/Rac GTPase-activating protein activity. J Biol Chem. 1995 Sep. 22; 270(38):22473-7.
40. Hinoi T, Kishida S, Koyama S, Ikeda M, Matsuura Y, Kikuchi A. Post-translational modifications of Ras and Ral are important for the action of Ral GDP dissociation stimulator. J Biol Chem. 1996 Aug. 16; 271(33):19710-6.
41. Nakashima S, Morinaka K, Koyama S, Ikeda M, Kishida M, Okawa K, Iwamatsu A, Kishida S, Kikuchi A. Small G protein Ral and its downstream molecules regulate endocytosis of EGF and insulin receptors. EMBO J. 1999 Jul. 1; 18(13):3629-42.
42. Yamaguchi A, Urano T, Goi T, Feig L A. An Eps homology (EH) domain protein that binds to the Ral-GTPase target, RalBP1. J Biol Chem. 1997 Dec. 12; 272(50):31230-4.
43. Morinaka K, Koyama S, Nakashima S, Hinoi T, Okawa K, Iwamatsu A, Kikuchi A. Epsin binds to the EH domain of POB1 and regulates receptor-mediated endocytosis. Oncogene. 1999 Oct. 21; 18(43):5915-22.
44. Jullien-Flores V, Mahe Y, Mirey G, Leprince C, Meunier-Bisceuil B, Sorkin A, Camonis J H. RLIP76, an effector of the GTPase Ral, interacts with the AP2 complex: involvement of the Ral pathway in receptor endocytosis. J Cell Sci. 2000 August; 113(Pt 16):2837-44.

45. Rosse C, L'Hoste S, Offner N, Picard A, Camonis J. RLIP, an effector of the Ral GTPases, is a platform for Cdk1 to phosphorylate epsin during the switch off of endocytosis in mitosis. J Biol Chem. 2003 Aug. 15; 278(33):30597-604.
46. Kashatus D F, Lim K H, Brady D C, Pershing N L, Cox A D, Counter C M. RALA and RALBP1 regulate mitochondrial fission at mitosis. Nat Cell Biol. 2011 Aug. 7; 13(9):1108-15.
47. Fillatre J, Delacour D, Van Hove L, Bagarre T, Houssin N, Soulika M, Veitia R A, Moreau J. Dynamics of the subcellular localization of RalBP1/RLIP through the cell cycle: the role of targeting signals and of protein-protein interactions. FASEB J. 2012 May; 26(5):2164-74.
48. Lee S, Wurtzel J G, Singhal S S, Awasthi S, Goldfinger L E. RALBP1/RLIP76 depletion in mice suppresses tumor growth by inhibiting tumor neovascularization. Cancer Res. 2012; 72(20):5165-73.
49. Lee S, Goldfinger L E. RLIP76 regulates HIF-1 activity, VEGF expression and secretion in tumor cells, and secretome transactivation of endothelial cells. FASEB J. 2014 September; 28(9):4158-68.
50. Wurtzel J G, Lee S, Singhal S S, Awasthi S, Ginsberg M H, and Goldfinger L E. RLIP76 regulates Arf6-dependent cell spreading and migration by linking ARNO with activated R-Ras at recycling endosomes. Biochem Biophys Res Commun. 2015; 467: 785-791.
51. Burg D, Mulder G J. Glutathione conjugates and their synthetic derivatives as inhibitors of glutathione-dependent enzymes involved in cancer and drug resistance. Drug Metab Rev. 2002 November; 34(4):821-63.
52. Milkovic L, Cipak Gasparovic A, Zarkovic N. Overview on major lipid peroxidation bioactive factor 4-hydroxynonenal as pluripotent growth-regulating factor. Free Radic Res. 2015; 49(7):850-60.
53. Prasanna P G S, Narayanan D, Hallett K, Bernhard E J, Ahmed M M, Evans G, Vikram B, Weingarten M, Coleman N. Radioprotectors and radiomitigators for improving radiation therapy: The Small Business Innovation Research (SBIR) Gateway for Accelerating Clinical Translation. Radiat Res. 2015 September; 184(3): 235-248.
54. Morris S M, Akerman G S, Desai V G, Tsai C A, Tolleson W H, Melchior W B Jr, Lin C J, Fuscoe J C, Casciano D A, Chen J J. Effect of p53 genotype on gene expression profiles in murine liver. Mutat Res. 2008 Apr. 2; 640(1-2):54-73.
55. Uren A G, Kool J, Matentzoglu K, de Ridder J, Mattison J, van Uitert M, Lagcher W, Sie D, Tanger E, Cox T, Reinders M, Hubbard T J, Rogers J, Jonkers J, Wessels L, Adams D J, van Lohuizen M, Berns A. Large-scale mutagenesis in p19(ARF)- and p53-deficient mice identifies cancer genes and their collaborative networks. Cell. 2008 May 16; 133(4):727-41.
56. Kulis M, Esteller M. DNA methylation and cancer. Advances in genetics. 2010; 70:27-56.
57. Bates S, Phillips A C, Clark P A, Stott F, Peters G, Ludwig R L, Karen H V. p14ARF links the tumor suppressors Rb and p53. Nature, 1998; 395:124-125.
58. Tavana O, Gu W. p53 and DNA methylation suppress the TRAIN to cell death. Cell Cycle. 2013 Jan. 1; 12(1): 9-10.
59. Ames B N, Shigenaga M K, Gold L S. DNA lesions, inducible DNA repair, and cell division: three key factors in mutagenesis and carcinogenesis. Environ Health Perspect. 1993 December; 101 Suppl 5:35-44.
60. Deferme L, Wolters J E, Claessen S M, Theunissen D H, van den Beucken T, Wagner J R, van Breda S G, Kleinjans J C, Briedé J J. Dynamic Interplay between the Transcriptome and Methylome in Response to Oxidative and Alkylating Stress. Chem Res Toxicol. 2016 Sep. 19; 29(9):1428-38.
61. Esterbauer H, Schaur R J, Zollner H. Chemistry and biochemistry of 4-hydroxynonenal, malonaldehyde and related aldehydes. Free Radic Biol Med. 1991; 11(1):81-128.
62. Shigenaga M K, Gimeno C J, Ames B N. Urinary 8-hydroxy-2'-deoxyguanosine as a biological marker of in vivo oxidative DNA damage. Proc Natl Acad Sci USA. 1989 December; 86(24):9697-701.
63. Li, Q., and Martinez, J. D. P53 is transported into the nucleus via an Hsf1-dependent nuclear localization mechanism. Mol. Carcinogenesis. 2011; 50:143-152.
64. Hu Y, Mivechi N F. HSF-1 interacts with Ral-binding protein 1 in a stress-responsive, multiprotein complex with HSP90 in vivo. J Biol Chem. 2003 May 9; 278(19): 17299-306.
65. Min J N, Huang L, Zimonjic D B, Moskophidis D, Mivechi N F. Selective suppression of lymphomas by functional loss of Hsf1 in a p53-deficient mouse model for spontaneous tumors. Oncogene. 2007 Aug. 2; 26(35): 5086-97.
66. Wang S S, Purdue M P, Cerhan J R, Zheng T, Menashe I, Armstrong B K, Lan Q, Hartge P, Kricker A, Zhang Y, Morton L M, Vajdic C M, Holford T R, Severson R K, Grulich A, Leaderer B P, Davis S, Cozen W, Yeager M, Chanock S J, Chatterjee N, Rothman N. Common gene variants in the tumor necrosis factor (TNF) and TNF receptor superfamilies and NF-kB transcription factors and non-Hodgkin lymphoma risk. PLoS One. 2009; 4(4): e5360.
67. Enari M, Ohmori K, Kitabayashi I, Taya Y. Requirement of clathrin heavy chain for p53-mediated transcription. Genes Dev. 2006 May 1; 20(9):1087-99.
68. Endo Y, Sugiyama A, Li S A, Ohmori K, Ohata H, Yoshida Y, Shibuya M, Takei K, Enari M, Taya Y. Regulation of clathrin-mediated endocytosis by p53. Genes Cells. 2008 April; 13(4):375-86.
69. Li R, Li Y, Kristiansen K, Wang J. SOAP: short oligonucleotide alignment program. Bioinformatics. 2008; 24:713-714.
70. Zhou Y, Lin N, Zhang B. An iteration normalization and test method for differential expression analysis of RNA-Seq data. BioData Min. 2014; 7:15.
71. Zhao, S., Fung-Leung, W. P., Bittner, A., Ngo, K., and Liu, X. Comparison of RNA-Seq and microarray in transcriptome profiling of activated T cells. PLOS One. 2014; 9:e78644
72. Huang da W, Sherman, B T, Lempicki, R A. Systematic and integrative analysis of large gene lists using DAVID bioinformatics resources. Nature protocols. 2009; 4, 44-57, doi:10.1038/nprot.2008.211.

The embodiments above are intended to be illustrative and not limiting. Additional embodiments are within the claims. In addition, although the present disclosure has been described with reference to particular embodiments, those skilled in the art will recognize that changes can be made in form and detail without departing from the spirit and scope of the disclosure. Any incorporation by reference of documents above is limited such that no subject matter is incorporated that is contrary to the explicit disclosure herein.

I claim:

1. A method of treating cancer in a Li-Fraumeni patient, the method comprising administering an effective amount of a composition comprising an anti-RLIP polyclonal antibody into the patient to partially inhibit RLIP76 in the patient.

2. The method of claim 1, wherein the composition further comprises a pharmaceutically acceptable carrier.

3. The method of claim 1, wherein the composition administration is repeated at predetermined intervals to effect chronic partial inhibition of RLIP76 in the patient such that the cancer treatment can be sustained chronically.

4. The method of claim 1, wherein the anti-RLIP polyclonal antibody is an anti-RLIP$^{171-185}$ polyclonal antibody.

5. A method of treating cancer in a p53 deficient living subject, the method comprising administering an effective amount of a composition comprising an anti-RLIP polyclonal antibody into the living subject to partially inhibit RLIP76 in the living subject.

6. The method of claim 5, wherein the composition further comprises a pharmaceutically acceptable carrier.

7. The method of claim 5, wherein the composition administration is repeated at predetermined intervals to effect chronic partial inhibition of RLIP76 in the living subject such that the cancer treatment can be sustained chronically.

8. The method of claim 5, wherein the living subject is a human.

9. The method of claim 5, wherein the anti-RLIP polyclonal antibody is an anti-RLIP$^{171-185}$ polyclonal antibody.

10. A method for reversion of DNA-methylation abnormalities caused by lack of p53 in a p53 deficient living subject by at least 50%, the method comprising administering an effective amount of composition comprising an anti-RLIP polyclonal antibody into the living subject to at least partially inhibit RLIP76 in the living subject.

11. The method of claim 10, wherein the composition further comprises a pharmaceutically acceptable carrier.

12. The method of claim 10, wherein the composition administration is repeated at predetermined intervals to effect chronic partial inhibition of RLIP76 in the living subject such that the DNA-methylation abnormalities caused by lack of p53 is reversed to normal chronically.

13. The method of claim 10, wherein the anti-RLIP polyclonal antibody is an anti-RLIP$^{171-185}$ polyclonal antibody.

* * * * *

UNITED STATES PATENT AND TRADEMARK OFFICE
CERTIFICATE OF CORRECTION

PATENT NO. : 11,427,816 B2
APPLICATION NO. : 15/684508
DATED : August 30, 2022
INVENTOR(S) : Sanjay Awasthi Page 1 of 1

It is certified that error appears in the above-identified patent and that said Letters Patent is hereby corrected as shown below:

In the Specification

Column 1, Line 6:
Delete "This invention was made with government support under grant number P30CA33572 awarded by the City of Hope National Medical Center and its Cancer Center Support Grant from the National Cancer Institute of the National Institutes of Health. The government has certain rights in the invention." and replace with:
-- This invention was made with government support under grant number P30CA033572 awarded by the City of Hope National Medical Center and its Cancer Center Support Grant from the National Cancer Institute of the National Institutes of Health. The government has certain rights in the invention. --

Signed and Sealed this
Twenty-seventh Day of May, 2025

Coke Morgan Stewart
*Acting Director of the United States Patent and Trademark Office*

SEQUENCE LISTING

<160> NUMBER OF SEQ ID NOS: 15

<210> SEQ ID NO 1
<211> LENGTH: 15
<212> TYPE: PRT
<213> ORGANISM: artificial sequence
<220> FEATURE:
<223> OTHER INFORMATION: Rlip Epitope AA171-185

<400> SEQUENCE: 1

Lys Pro Ile Gln Glu Pro Glu Val Pro Gln Ile Asp Val Pro Asn
1               5                   10                  15

<210> SEQ ID NO 2
<211> LENGTH: 21
<212> TYPE: DNA
<213> ORGANISM: artificial sequence
<220> FEATURE:
<223> OTHER INFORMATION: Rlip Antisense R508

<400> SEQUENCE: 2
ggctcctgaa ttggcttttt c                                           21

<210> SEQ ID NO 3
<211> LENGTH: 23
<212> TYPE: RNA
<213> ORGANISM: artificial sequence
<220> FEATURE:
<223> OTHER INFORMATION: sense siRNA for targeted cDNA
<220> FEATURE:
<221> NAME/KEY: d
<222> LOCATION: (22)..(23)
<223> OTHER INFORMATION: dT

<400> SEQUENCE: 3
gaaaaagcca auucaggagc cdd                                         23

<210> SEQ ID NO 4
<211> LENGTH: 23
<212> TYPE: RNA
<213> ORGANISM: artificial sequence
<220> FEATURE:
<223> OTHER INFORMATION: Rlip mRNA

<400> SEQUENCE: 4
ggcuccugaa uuggcuuuuu cuu                                         23

<210> SEQ ID NO 5
<211> LENGTH: 23
<212> TYPE: DNA
<213> ORGANISM: artificial sequence
<220> FEATURE:
<223> OTHER INFORMATION: Rlip cDNA

<400> SEQUENCE: 5
aagaaaaagc caattcagga gcc                                         23

<210> SEQ ID NO 6
<211> LENGTH: 23
<212> TYPE: RNA
<213> ORGANISM: artificial sequence
<220> FEATURE:
<223> OTHER INFORMATION: antisense siRNA
<220> FEATURE:
<221> NAME/KEY: d
<222> LOCATION: (22)..(23)
<223> OTHER INFORMATION: dT

<400> SEQUENCE: 6
ggcuccugaa uuggcuuuuu cdd                                    23

<210> SEQ ID NO 7
<211> LENGTH: 21
<212> TYPE: DNA
<213> ORGANISM: artificial sequence
<220> FEATURE:
<223> OTHER INFORMATION: control scrambled phosphorothioate
      oligonucleotide (CAS)

<400> SEQUENCE: 7
catcgaaatc gttgcagtta c                                      21

<210> SEQ ID NO 8
<211> LENGTH: 21
<212> TYPE: DNA
<213> ORGANISM: artificial sequence
<220> FEATURE:
<223> OTHER INFORMATION: internal control primer sequence for ZZZ3

<400> SEQUENCE: 8
agaccattgc tgtacttgag g                                      21

<210> SEQ ID NO 9
<211> LENGTH: 21
<212> TYPE: DNA
<213> ORGANISM: artificial sequence
<220> FEATURE:
<223> OTHER INFORMATION: internal control primer sequence for ZZZ3

<400> SEQUENCE: 9
ggtatggaag ccctatgtca g                                      21

<210> SEQ ID NO 10
<211> LENGTH: 25
<212> TYPE: DNA
<213> ORGANISM: artificial sequence
<220> FEATURE:
<223> OTHER INFORMATION: forward primer sequences of PTPN6

<400> SEQUENCE: 10
atttaaggtg gatgatggtg ttatt                                  25

<210> SEQ ID NO 11
<211> LENGTH: 27
<212> TYPE: DNA
<213> ORGANISM: artificial sequence
<220> FEATURE:
<223> OTHER INFORMATION: reverse primer sequences of PTPN6

<400> SEQUENCE: 11
tccaaaactc aaaaaacttc tataacc                                27

<210> SEQ ID NO 12
<211> LENGTH: 25
<212> TYPE: DNA
<213> ORGANISM: artificial sequence
<220> FEATURE:
<223> OTHER INFORMATION: forward primer sequence of HOXA5

<400> SEQUENCE: 12
gtttgatgat ttttagaggt aaatt                                  25

<210> SEQ ID NO 13

```
<211> LENGTH: 25
<212> TYPE: DNA
<213> ORGANISM: artificial sequence
<220> FEATURE:
<223> OTHER INFORMATION: reverse primer sequence of HOXA5

<400> SEQUENCE: 13
ccataataaa ctataacctc aattc                                              25

<210> SEQ ID NO 14
<211> LENGTH: 23
<212> TYPE: RNA
<213> ORGANISM: artificial sequence
<220> FEATURE:
<223> OTHER INFORMATION: sequence of the scrambled siRNA in the sense
      direction
<220> FEATURE:
<221> NAME/KEY: d
<222> LOCATION: (22)..(23)
<223> OTHER INFORMATION: dT

<400> SEQUENCE: 14
guaacugcaa cgauuucgau gdd                                                23

<210> SEQ ID NO 15
<211> LENGTH: 23
<212> TYPE: RNA
<213> ORGANISM: artificial sequence
<220> FEATURE:
<223> OTHER INFORMATION: sequence of the scrambled siRNA in the
      antisense direction
<220> FEATURE:
<221> NAME/KEY: d
<222> LOCATION: (22)..(23)
<223> OTHER INFORMATION: dT

<400> SEQUENCE: 15
caucgaaauc guugcaguua cdd                                                23
```